United States Patent [19]
Capelli

[11] Patent Number: 6,093,414
[45] Date of Patent: Jul. 25, 2000

[54] SILVER-BASED ANTIMICROBIAL COMPOSITIONS

[75] Inventor: Christopher C. Capelli, 311 Hawthorn Ave., Marshfield, Wis. 54449

[73] Assignee: Christopher C. Capelli, Kenosha, Wis.

[21] Appl. No.: 08/909,239

[22] Filed: Aug. 11, 1997

[51] Int. Cl.[7] .......................... A01N 25/00; A61K 33/38; A61K 31/65; A61K 31/56
[52] U.S. Cl. .................. 424/405; 424/618; 514/152; 514/179; 514/192; 514/199; 514/535
[58] Field of Search ...................... 424/405, 618; 514/179, 535, 152, 192, 199

[56] References Cited

U.S. PATENT DOCUMENTS

| | | | |
|---|---|---|---|
| 3,761,590 | 9/1973 | Fox | 424/228 |
| 5,326,567 | 7/1994 | Capelli | 424/405 |
| 5,429,819 | 7/1995 | Oka et al. | 424/400 |
| 5,651,978 | 7/1997 | Tomioka et al. | 424/421 |
| 5,662,913 | 9/1997 | Capelli | 424/405 |
| 5,744,151 | 4/1998 | Capelli | 424/405 |

OTHER PUBLICATIONS

Tomioka et al., "Synthesis of Antimicrobial Agent Composed of Silver–Thiosulfate Complex Ion," *Nippon Kagaku Kaishi* 10:848–50 (1995).
Russell et al., Antimicrobial Activity and Action of Silver, *Progress in Medicinal Chemistry* 31:351–70 (1994).
Dooly et al., "Multidrug–resistant tuberculosis," *Ann. Int. Med.* 117:257–59 (1992).
Nadler, "Multidrug resistant tuberculosis," *N. Eng. J. Med.* 327:1172–75 (1992).

*Primary Examiner*—Kevin E. Weddington
*Attorney, Agent, or Firm*—Medlen & Carroll, LLP

[57] ABSTRACT

The present invention relates generally to silver-based antimicrobial compositions and processes for making such compositions. More particularly, the present invention describes stable, purified silver-based antimicrobial compositions, and processes for making such compositions, comprising carrier-free silver thiosulfate ion complexes either suspended in a base or incorporated into a matrix. These silver thiosulfate ion complex antimicrobial compositions are useful in the treatment and prevention of infections and diseases.

38 Claims, No Drawings

SILVER-BASED ANTIMICROBIAL COMPOSITIONS

FIELD OF INVENTION

The present invention relates to silver-based antimicrobial compositions and processes for making such compositions that are suitable for use in the treatment and prevention of infections.

BACKGROUND OF THE INVENTION

1. Antimicrobial Agents

Antimicrobial agents are chemical compounds that either destroy microbes, prevent their pathogenic action, or prevent their growth. Antimicrobial agents, often referred to as anti-infective agents, are frequently applied topically to the skin and mucous membranes in the form of a solution, cream, or ointment; appropriate formulations may be applied to wounds and body cavities, and to the eyes, nose, and mouth.

In general, topical antimicrobial agents are directed at bacteria, viruses, and fungi. They have been used successfully in the prevention and treatment of a number of infections, including impetigo, candidiasis, tinea pedis (athlete's foot), acne vulgaris, and infections resulting from burns and surgical wounds.

Most agents have a limited spectrum of activity. For example, some are specific for particular gram (+) organisms, while others are specific for particular gram (−) organisms. Moreover, bactericidal agents typically are not fungicidal, while fungicidal agents typically are not bactericidal.

In addition, due to the widespread use and frequent over-prescribing of antimicrobial agents, there is an increasing incidence of microbes acquiring drug-resistance. In other words, a microbe that was once susceptible (i.e., inhibited or killed) to a particular antimicrobial agent is no longer susceptible. This is especially important with regard to bacteria.

Acquired drug resistance is usually caused by a mutation within the genome of the microbe or by the acquisition of a plasmid. For example, one of the major mechanisms of resistance to the β-lactam antibiotics, including penicillins, is the production of β-lactamases. Moreover, resistance to one member of a class of agents (e.g., the aminopenicillin ampicillin) can result in complete cross-resistance to other members of that class (e.g., the aminopenicillin amoxicillin).

II. Topical Silver-Containing Agents

A. Currently Used Therapeutic Agents

Two formulations containing silver have been utilized for therapeutic purposes, silver nitrate and silver sulfadiazine. As set forth hereafter, each is associated with potentially severe adverse effects and other limitations.

A 1% silver nitrate ophthalmic solution can be used in newborns for the prophylaxis of gonococcal ophthalmia (gonococcal ophthalmia neonatorum). Because the silver ion is precipitated by chloride, the silver nitrate solution does not readily penetrate into tissue. Unfortunately, the silver salts stain tissue black as a result of the deposition of reduced silver; some of the staining may persist indefinitely. Thus, silver nitrate is not used topically for other indications (e.g., impetigo).

Silver sulfadiazine 1% topical cream is routinely used as an adjunct in the prevention and treatment of infection in burn victims. [See U.S. Pat. No. 3,761,590 to Fox, hereby incorporated by reference]. Silver sulfadiazine, produced by the reaction of silver nitrate with sulfadiazine, has been associated with necrosis of the skin. In addition, sulfadiazine may accumulate in patients with impaired hepatic or renal function, requiring in severe cases examination of the patient's urine for sulfonamide crystals. Moreover, patients allergic to sulfa agents may exhibit cross-hypersensitivity with silver sulfadiazine. [See generally, *AHFS Drug Information*, Gerald K. McKevoy, ed., pp. 1704–05 and 2215–16 (1993)].

B. Newer Antimicrobial Silver-Containing Compositions

One of the reasons why there are few commercially available silver-containing therapeutic formulations is the difficulty of making such formulations photostable. That is, such formulations turn a dark color and frequently lose antimicrobial efficacy upon short-term (e g., 3–4 days) exposure to ambient light.

There have been several recent efforts to produce a silver-containing formulation that exhibits high antimicrobial efficacy and photostability. For example, U.S. Pat. No. 5,326,567 to Capelli, hereby incorporated by reference, describes an antimicrobial composition comprising a stabilizing acyclic polyether polymer, silver ion, and a stabilizing halide. The composition may be used in several manners, including topical application to a subject and incorporation into a medical device.

In addition, a new class of silver-containing agents, the silver thiosulfate ion complexes, has recently been disclosed in U.S. Pat. No. 5,429,819 to Oka el al. (hereafter "the Oka Patent"), hereby incorporated by reference. [See also Tomioka et al., "Synthesis of Antimicrobial Agent Composed of Silver-Thiosulfate Complex Ion," Nippon Kagaku Kaishi 10:848–50 (1995)]. The Oka Patent describes an antiviral composition that contains i) a thiosulfate salt and ii) at least one thiosulfate complex salt of a metal and iii) a porous particulate carrier; the metal is either silver, copper or zinc, and the salts are carried on the porous particulate carrier. According to the Oka Patent's teachings, the thiosulfate complex salt and thiosulfate metal complex salt are first prepared as a solution. Thereafter, a porous carrier such as silica gel is impregnated with the solution. Finally, the thiosulfate complex and thiosulfate metal complex salt are immobilized on the porous carrier through drying. This metal-containing porous carrier is then formulated into the compositions described in the Oka Patent.

The antimicrobial compositions taught in the Oka Patent are associated with several notable shortcomings. First, the silver thiosulfate ion complex compositions contain a relatively large concentration of waste salts, resulting from the complexation of a thiosulfate salt, sulfite salt, and a silver salt, and are thus relatively impure. For example, producing 1 part of a silver thiosulfate ion complex using 1 part of silver nitrate (or silver acetate) to 2 parts sodium thiosulfate and/or 2 parts sodium sulfite will result in 1 part waste sodium nitrate (or sodium acetate); the inclusion of these salts results in a lower concentration of silver. Similarly, as indicated above, the silver thiosulfate ion complex requires the use of porous carrier particles; the necessity of these carrier particles limits the concentration of thiosulfate complex salt and thiosulfate metal complex salt. Thus, the amount of porous carrier particles needed to provide silver at antimicrobial concentrations is high, and, as a result, a topical antimicrobial composition would feel gritty and would be irritating to the skin or wound. In addition, if the concentration of thiosulfate complex salt and thiosulfate metal complex salt carried on the porous carrier is too high, the composition may discolor.

Finally, the compositions taught by the Oka Patent cannot be easily incorporated into a polymer matrix at high concentrations. As stated above, incorporation of silver at antimicrobial concentrations requires concomitant incorporation of a large amount of porous carrier. This can cause undesirable changes in the polymer matrix' physical properties (e.g., a hydrocolloid matrix that is stiff and less absorptive). In addition, such incorporation can be unwieldy. For example, in an alginate matrix containing water-insoluble fibers, the silver-containing porous carrier cannot be incorporated into the alginate fibers; as a result, the porous carrier must be mixed loosely within the alginate fibers. Unfortunately, the porous carrier can fall out when the alginate matrix is handled.

From the above, it should be clear that the commercially-available silver-based antimicrobial agents have limited applications and can be associated with severe adverse effects. Moreover, many recent efforts to develop a topical silver-containing formulation are connected with drawbacks, as exemplified by the prior art requirement of a carrier. What is needed is a stable silver-containing antimicrobial composition which is suitable for use in the treatment and prevention of a broad range of infections and that is not associated with the adverse effects and limitations of the agents that have previously been described.

SUMMARY OF THE INVENTION

The present invention relates generally to silver-based antimicrobial compositions and processes for making such compositions suitable for use in the treatment and prevention of infections. In particular, the present invention relates to stable silver-based antimicrobial compositions, and processes for making such compositions, comprising carrier-free, suspended silver thiosulfate ion complexes in a base. Preferably, the silver thiosulfate ion complexes are homogeneously suspended in an anhydrous base. Alternatively, the silver thiosulfate ion complexes of the present invention can be incorporated into a matrix and used with a medical device. Pharmaceutical compositions can also be produced by combining the silver thiosulfate ion complexes with medicinal agents, including but not limited to antimicrobial agents, steroids, and anesthetics.

One advantage of providing silver thiosulfate ion complexes in a carrier-free form is the ability to produce antimicrobial compositions containing high concentrations of silver thiosulfate ion complexes so as to provide potent antimicrobial activity. A further advantage of the carrier-free compositions is the elimination of irritation that may result from the carrier upon topical administration. Thus, the invention contemplates a method of treating or preventing infections in comprising applying topically to the site (or potential site) of infection an effective amount of the foregoing composition.

As alluded to above, the invention also contemplates methods of making the stable silver-based antimicrobial compositions. It is preferred that the silver complexes of the present invention are derived from the complexation of silver cations from silver halides (preferably silver chloride) with anions from the sodium thiosulfate salts; the molar ratio of the thiosulfate anions to the silver cations is preferably at least 1:1 and more preferably at least 1.3:1. It is desirable that the silver thiosulfate ion complexes are solid and essentially pure, i.e., they do not contain significant amounts of waste salts or other substances that interfere with their antimicrobial activity; in addition, they do not require carrier particles.

The compositions are able to contain high concentrations of silver thiosulfate ion complexes, thereby providing strong antimicrobial activity. Moreover, the compositions may be used in combination with other pharmaceutical (e.g., topical) agents (e.g., BACTROBAN® [mupirocin], SmithKline Beecham). Such combination may serve to avoid antimicrobial resistance, increase the spectrum of activity, and have a synergistic effect.

The silver thiosulfate ion complexes of the present invention may be incorporated into medical devices, including medical implants, wound care devices, body cavity and personal protection devices, and the like. By way of illustration, purified silver thiosulfate ion complexes may be incorporated with an anhydrous polymer matrix that is used to coat a urinary catheter in order to prevent infection. Similarly, the silver thiosulfate ion complexes may be used in cosmetics and personal care products to make them resistant to antimicrobial contamination. Examples of cosmetics include lipsticks and glosses, lip pencils, mascaras, eye liners, eye shadows, moisturizers, liquid and powder makeup foundations, powder and cream blushes, perfumes, colognes, various creams and toners, etc., and assorted applicators like combs, brushes, sponges, and cotton swabs and balls, and examples of personal care products include deodorants, razors, shaving creams, shampoos, conditioners, various hair treatments like mousses and sprays, toothpastes, mouthwashes, dental flosses and tapes, sunscreens, moisturizers, tampons, sanitary napkins, panty shields, diapers, baby wipes, facial tissues, toilet tissues, etc.

The present invention contemplates a composition, comprising carrier-free suspended silver thiosulfate ion complexes suspended in a base. In one embodiment, the base is anhydrous. It is contemplated that the concentration of silver thiosulfate ion complexes within the base is sufficient to provide a therapeutic benefit. Specifically, the present invention contemplates concentrations of silver thiosulfate ion complexes within the base from 0.01% to 30% (w/w) and from 0.1% to 3.0% (w/w). The preferred concentration of silver thiosulfate ion complexes within the base is from 0.2% to 1.5% (w/w). In one embodiment, the base is selected from the group consisting of polyethylene glycol, AQUAPHOR® (an ointment base comprising Petrolatum, Mineral Oil, Ceresin, and Lanolin Alcohol), and white petrolatum.

The present invention also contemplates a method of treating or preventing a topical microbial infection, comprising the steps of a) providing i) a subject infected with a topical microbial infection and ii) an effective amount of carrier-free suspended silver thiosulfate ion complexes in a base; and b) administering topically the effective amount of the carrier-free suspended silver thiosulfate ion complexes in a base to the subject, thereby treating or preventing the topical microbial infection. In one embodiment, the base is anhydrous.

It is contemplated that the concentration of silver thiosulfate ion complexes within the base is sufficient to provide a therapeutic benefit. For example, the present invention specifically contemplates concentrations of silver thiosulfate ion complexes within the base from 0.01% to 30% (w/w) and from 0.1% to 3.0% (w/w). The preferred concentration of silver thiosulfate ion complexes within the base is from 0.2% to 1.5% (w/w). In one embodiment, the base is selected from the group consisting of polyethylene glycol, AQUAPHOR® (an ointment base comprising Petrolatum, Mineral Oil, Ceresin, and Lanolin Alcohol), and white petrolatum.

The present invention further contemplates a method of imparting antimicrobial protection to an object, comprising the steps of: a) providing i) an object and ii) an effective amount of carrier-free suspended silver thiosulfate ion complexes; and b) applying the effective amount of the carrier-free suspended silver thiosulfate ion complexes in a base to the object, thereby imparting antimicrobial protection to the object. It is preferred that the object is solid and chemically inert.

In one embodiment, the concentration of silver thiosulfate ion complexes is sufficient to provide a therapeutic benefit. Specifically, the present invention contemplates concentrations of silver thiosulfate ion complexes from 0.01% to 30% (w/w) and from 0.1% to 3.0% (w/w). The preferred concentration of silver thiosulfate ion complexes is from 0.2% to 1.5% (w/w).

In still further embodiments, the object is a medical device. In particular embodiments, the medical device comprises a matrix. In some embodiments the matrix is a polymer, while it is anhydrous in still further embodiments.

The present invention also contemplates a process for producing essentially anhydrous silver thiosulfate ion complexes, comprising: a) making an aqueous solution of silver thiosulfate ion complexes; b) adding a solvent to the solution to create a biphasic separation wherein the silver thiosulfate ion complexes separate into one phase; c) collecting the phase containing the silver thiosulfate ion complexes; and d) removing water from the collected phase such that the silver thiosulfate ion complexes are essentially anhydrous. In particular embodiments, the ratio of thiosulfate ions to silver ions is greater than or equal to 2:1 and preferably less than 3:1.

In some embodiments, the aqueous solution of silver thiosulfate ion complexes is formed by reacting a silver halide and sodium thiosulfate. In other embodiments, the molar ratio of silver cations from the silver halide to thiosulfate anions from the sodium thiosulfate is preferably at least 1:1 and more preferably at least 1.3:1. In still further embodiments, the silver halide is silver chloride.

In other embodiments, the solvent is water-miscible. The solvent is selected from the group consisting of ethyl alcohol, isopropyl alcohol, methyl alcohol, acetone, and tetrahydrofuran in certain embodiments.

Additionally, the present invention contemplates a process for producing essentially anhydrous silver thiosulfate ion complexes, comprising: a) making an aqueous solution of silver thiosulfate ion complexes; b) adding a solvent to the solution to precipitate the silver thiosulfate ion complexes; c) collecting the precipitated silver thiosulfate ion complexes; and d) removing water from the collected silver thiosulfate ion complexes such that the silver thiosulfate ion complexes are essentially anhydrous. In particular embodiments, the ratio of thiosulfate ions to silver ions is less than 2:1 and preferably greater than 1:1.

In some embodiments, the aqueous solution of silver thiosulfate ion complexes is formed by reacting a silver halide and sodium thiosulfate. In other embodiments, the molar ratio of silver cations from the silver halide to thiosulfate anions from the sodium thiosulfate is preferably at least 1:1 and more preferably at least 1.3:1. In still further embodiments, the silver halide is silver chloride.

In other embodiments, the solvent is water-miscible. The solvent is selected from the group consisting of ethyl alcohol, isopropyl alcohol, methyl alcohol, acetone, and tetrahydrofuran in certain embodiments.

The present invention also contemplates a pharmaceutical mixture, comprising: a) a medicinal agent; and b) silver thiosulfate ion complexes. In preferred embodiments, the silver thiosulfate ion complexes are carrier-free. In particular embodiments, the pharmaceutical mixture further comprises an anhydrous base; in some embodiments, the base is selected from the group consisting of polyethylene glycol, AQUAPHOR® (an ointment base comprising Petrolatum, Mineral Oil, Ceresin, and Lanolin Alcohol), and white petrolatum.

In some embodiments of the present invention, the concentration of the silver thiosulfate ion complexes in the pharmaceutical mixture is from 0.01% to 30% (weight to weight). In further embodiments, the concentration of silver thiosulfate ion complexes is from 0.1% to 3.0% (weight to weight), while in still further embodiments the concentration is from 0.2% to 1.5% (weight to weight).

In particular embodiments, the medicinal agent of the pharmaceutical mixture is an antimicrobial agent. In some embodiments, the antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline. When the medicinal agent is an antimicrobial agent, in some embodiments the pharmaceutical mixture has a broader spectrum of antimicrobial protection than the silver thiosulfate ion complexes.

Furthermore, the medicinal agent of the pharmaceutical mixture is a steroid in certain embodiments. In particular embodiments, the steroid is selected from the group consisting of betamethasone benzoate, betamethasone valerate, desonide, fluocinolone acetonide, halcinonide, hydrocortisone, and metandienone.

Finally, the medicinal agent of the pharmaceutical mixture is an anesthetic in still other embodiments. In certain embodiments, the anesthetic is selected from the group consisting of benzocaine, dibucaine, lidocaine, pramoxine hydrochloride and tetracacine.

DEFINITIONS

To facilitate understanding of the invention set forth in the disclosure that follows, a number of terms are defined below.

The term "carrier" refers to a substance, like an inorganic oxide, in which a material can be impregnated and then, if necessary, immobilized through drying. For example, the Oka Patent describes the impregnation of a porous particulate carrier (e.g., silica gel) with a solution containing thiosulfate complex salt and thiosulfate metal complex salt. In contrast, the term "carrier" does not refer to the mere suspension of materials like silver thiosulfate ion complexes in a base. The term "carrier-free" refers to being without such things as carrier particles, porous particulate carriers, and the like used as carriers for other materials. For example, the compositions of the present invention are "carrier-free" in that they comprise silver thiosulfate ion complexes that do not require such a carrier.

The term "base" refers to any substance useful for the suspension of the silver thiosulfate ion complexes of the present invention. In a preferred embodiment, the base is "anhydrous" (e.g., an ointment) and can be used to suspend a medicinal agent for topical administration. Useful anhydrous bases include, but are not limited to, white petrolatum, AQUAPHOR® (an ointment base comprising Petrolatum, Mineral Oil, Ceresin, and Lanolin Alcohol), and polyethylene glycol (PEG) polymers with molecular weights greater than 600. The preferred anhydrous base is a PEG ointment composition; an ointment made up of PEGs can absorb and associate with a small amount of water so that the water is not free to hydrolyze the thiosulfate ligand. It should be noted that some water is tolerable in the final product but that, generally speaking, the presence of water will reduce the shelf-life of the composition. For example, an anhydrous base which contains no water and few, if any, hydroxy or acid groups should have a shelf-life of many years, while a base containing small amounts of water (e.g., less than 5%) would have a shorter shelf-life (e.g., less than 6 months). If a PEG ointment base has a very small amount of water (e.g., much less than 1%), the silver thiosulfate ion complexes should be stable enough to provide the product with an acceptable shelf-life (e.g., greater than one year). In one embodiment, the base is semisolid.

The term "silver thiosulfate ion complexes" refers to the silver-containing material produced by the process of the present invention and incorporated into the compositions of the present invention. More specifically, the silver thiosulfate ion complexes are obtained by adding a silver halide, e.g., silver chloride, to an aqueous solution and then adding a thiosulfate salt, e.g., sodium thiosulfate, to the solution. Though the benefit provided by the complexes of the present invention is not limited by an understanding of the precise nature of the complexes, the chemical formula of the primary silver thiosulfate ion complexes formed when a large excess of thiosulfate salt is used is represented by $[Ag(S_2O_3)_3]^{5-}$. By comparison, the chemical formula of the primary silver thiosulfate ion complexes formed when only a small excess of thiosulfate salt is used is represented by $[Ag_2(S_2O_3)_3]^{4-}$. The preferred silver thiosulfate ion complexes are those represented by $[Ag_2(S_2O_3)_3]^{4-}$. The resulting silver thiosulfate ion complexes are in a relatively pure solid form, and are stable, highly water soluble and antimicrobially active.

The term "essentially anhydrous silver thiosulfate ion complexes" refers to silver thiosulfate ion complexes that may be essentially free of all remnant water, i.e., they may contain a small amount of water (generally less than 5% of the original amount of water present, preferably less than 1%, and most preferably less than 0.1%), provided that the water does not interfere with the antimicrobial function of the complexes.

The term "suspended" refers broadly to the dispersion (i.e., not dissolution) of material (e.g., silver thiosulfate ion complexes) in the base. The material is preferably finely divided and preferably dispersed homogeneously throughout the base.

The term "aqueous solution" refers to a liquid mixture containing, among other things, water.

The term "solvent" refers to a liquid that is capable of dissolving a substance. The term "water-miscible solvent" refers to a solvent that is capable of being mixed with water and remaining so after completion of the mixing process.

The term "phase" refers to a physically distinct and separable portion of a heterogeneous system. The term "biphasic separation" refers to the creation of two phases; generally speaking, a "biphasic separation" allows a material (e.g., silver thiosulfate ion complexes) to be partitioned into one of the resulting phases, thereby facilitating isolation of that material. As described in further detail below, the addition of an appropriate solvent (e.g., ethyl alcohol) to an aqueous solution of silver thiosulfate ion complexes results in a biphasic separation. A smaller, denser, liquid phase primarily contains the silver thiosulfate ion complexes associated with water; there is little, if any, solvent in this phase. A larger liquid phase primarily contains the waste salts and the solvent.

The terms "collecting," "collect" and the like refer to the general processes of isolating, partitioning, etc. one material from another. For example, a desired material may partition into one phase of a biphasic system; the phase containing that material (e.g., the silver thiosulfate ion complexes of the present invention) can be removed from the biphasic system using well known means (e.g., pipet and separatory funnel).

The term "removing" refers broadly to the use of methods for the complete or partial elimination of water from the phase containing the silver thiosulfate ion complexes (i.e., the collected phase). The present invention is not limited to any particular method; rather, generally known methods of removal (e.g., freeze drying, oven drying, evaporation, and solvent extraction) may be used in conjunction with the present invention.

The term "effective amount" refers to that amount of essentially anhydrous silver thiosulfate ion complexes that is required to provide some "therapeutic benefit". The present invention is not limited by the nature or scope of the therapeutic benefit provided. The degree of benefit may depend on a number of factors, e.g., the severity of a *S. aureus* infection and the immune status of the individual.

The term "therapeutic composition" refers to a composition that includes essentially anhydrous silver thiosulfate ion complexes in a pharmaceutically acceptable form. The characteristics of the form will depend on a number of factors, including the site of topical administration and the method by which the form will be used. For example, a composition for use in conjunction with personal care products must be formulated such that the composition retains its antimicrobial properties while not adversely affecting the characteristics of the personal care product itself. The therapeutic composition may contain diluents, adjuvants and excipients, among other things.

The terms "subject" and "host" refer to humans and animals.

The term "approximately" refers to the actual value being within a range of the indicated value. In general, the actual value will be between 5% (plus or minus) of the indicated value.

The terms "topical," "topically," and the like include, but are not limited to, the surface of the skin and mucosal tissue, in wounds, in the eyes, nose, mouth, anus and vagina.

The term "wound" includes a burn, cut sore, blister, rash or any other lesion or area of disturbed skin. The term "wound dressing" includes foam dressings, thin film dressings, burn dressings, surgical dressings, absorptive dressings, gauze, sheets or other types of medical device used to treat wounds.

The terms "microbe, "microbial," and the like include bacteria, fungi, and viruses. The terms "antimicrobial" and "antimicrobial activity" refer to the ability to kill or inhibit the growth of microbes.

The term "photostable" means that an object or material is resistant to discoloration when exposed to ambient light for a period of at least 72 hours.

The terms "matrix," "matrices" and the like refer broadly to materials in which the silver thiosulfate ion complexes of the present invention can be embedded in, attached to, or otherwise associated with. A "polymer matrix" is one type of matrix comprising one or more natural or synthetic compounds, usually of high molecular weight, in the form of repeated linked units. The term "anhydrous polymer matrix" refers to any solid material that may be free of water or that may contain a small amount of water (generally less than 5% by weight), provided that the water does not interfere with the antimicrobial function of the complexes carried by the matrix. The preferred anhydrous polymer matrix materials are materials compatible with the silver thiosulfate ion complexes of the present invention. The most preferred polymer matrix materials are those being compatible with the silver thiosulfate ion complexes and having some capacity to absorb and/or swell in the presence of water. Examples of anhydrous polymer matrix materials, include, but are not limited to, adhesives such as acrylic-based pressure sensitive adhesives; biopolymers such as silk; hydrocolloid materials such as sodium carboxymethylcellulose, either alone or when bound in a polymer; and polymers such as polyurethane in the form of coatings, films, foams, etc.

The term "medical device" refers broadly medical implants, wound care devices, body cavity and personal protection devices, and the like. Medical implants include, but are not limited to, urinary and intravascular catheters, dialysis shunts, wound drain tubes, skin sutures, vascular grafts and implantable meshes, intraocular devices, and heart valves. Wound care devices include, but are not limited to, general wound dressings, non-adherent dressings, burn dressings, biological graft materials, tape closures and dressings, and surgical drapes. Finally, body cavity and personal protection devices include, but are not limited to, tampons, sponges, surgical and examination gloves, toothbrushes, intrauterine devices, diaphragms, and condoms. The silver thiosulfate ion complexes of the present invention can be use to impart antimicrobial protection to objects including, but not limited to, medical devices.

The term "purified" means that the material has been subjected to a process (e.g., extraction) to remove impurities. Following the process, the material may be free from contamination of extraneous matter or, more commonly, only contain impurities at levels that do not interfere with the intended function. For example, it is advantageous to produce silver thiosulfate ion complexes that do not contain significant amounts of waste salts (e.g., sodium nitrate or sodium acetate); if such waste salts are incorporated into compositions or medical devices, they may be irritating to the skin or other tissue. In addition, they may reduce the concentration of antimicrobially active silver. For example, if the silver thiosulfate ion complexes are made using silver iodide silver salt and sodium thiosulfate salt, the resulting waste salt would be sodium iodide. The iodide ion would aggressively compete for the dissociated ("free") silver ion, resulting in reduced concentration of antimicrobially active silver.

DETAILED DESCRIPTION OF THE INVENTION

The present invention relates to silver-based antimicrobial compositions, and processes for making such compositions, that are suitable for use in the treatment and prevention of infections. In particular, the present invention relates to stable silver-based antimicrobial compositions, and processes for making such compositions, comprising carrier-free, suspended silver thiosulfate ion complexes in an a base, and silver thiosulfate ion complexes incorporated into an anhydrous polymer matrix and used with a medical device.

The description of the invention is divided into the following parts: I) Processes To Obtain Silver Thiosulfate Ion Complexes In A Solid Form; II) Compositions Containing Silver Thiosulfate Ion Complexes; III) Therapeutic Use Of Compositions Containing Silver Thiosulfate Ion Complexes, and IV) Incorporation Of Silver Thiosulfate Ion Complexes Into Matrices For Use In Medical Devices. Each of these parts will be discussed in turn.

I. Processes to Obtain Silver Thiosulfate Ion Complexes Material in a Solid Form As previously indicated, the compositions of the Oka Patent contain a thiosulfate salt, at least one thiosulfate salt of a metal, and a porous particulate carrier. The carrier was required because the thiosulfate salt and the thiosulfate salt of a metal can "hardly be obtained as a simple substance in a solid state". [Oka Patent, col. 2, 11. 45–46]. In contrast to the Oka Patent, the present invention is directed at a process for obtaining carrier-free silver thiosulfate ion complexes. Based on the prior art's acknowledged difficulty in obtaining silver thiosulfate ion complexes in a carrier-free solid state, the discovery of the process disclosed hereafter was both surprising and unexpected. Moreover, the process of the present invention also results in carrier-free silver thiosulfate ion complexes in high yields, another surprising and unexpected result.

The present invention contemplates the production of carrier-free silver thiosulfate ion complexes wherein the ratio of thiosulfate ion to silver ion is preferably at least 1.3 to 1. To optimize the antimicrobial effectiveness of the final products containing the silver thiosulfate ion complexes, it is preferable that the complexes be purified (e.g., subjected to methods to remove contaminants such as waste salts in an amount that adversely interferes with the silver concentration obtainable).

The present invention provides two processes of producing purified silver thiosulfate ion complexes from thiosulfate ions and silver ions. The first process is preferred when the ratio of thiosulfate ions to silver ions is greater than or equal to 2-to-1, and the second process is preferred when the ratio is less than 2-to-1.

A. Process for Producing Silver Thiosulfate Ion Complexes When the Ratio of Thiosulfate Ions to Silver Ions is Greater Than or Equal to 2-to-1

The process for producing essentially anhydrous silver thiosulfate ion complexes when the ratio of thiosulfate ions to silver ions is greater than 2-to-1 involves four major steps. The first step consists of making an aqueous solution of silver thiosulfate ion complexes. The aqueous solution of the silver thiosulfate ion complexes is obtained by first adding a silver halide, such as silver chloride, silver bromide, etc., to an aqueous solution. Thereafter, a thiosulfate salt, such as sodium thiosulfate or potassium thiosulfate, is added to the aqueous solution.

The use of a silver halide instead of another silver-containing molecule is preferred because the silver thiosulfate ion complexes produced are associated with increased short-term stability. This is especially important when the concentration of the silver thiosulfate ion complexes is high and/or the ratio of thiosulfate ions to silver ions is low. Likewise, the use of a silver halide promotes stability when making a solution of the silver thiosulfate ion complexes when the concentration of silver thiosulfate ion complexes in the resulting aqueous solution is high. As indicated above, when making silver thiosulfate ion complexes where the primary silver ion complexes formed is represented by the formula $[Ag(S_2O_3)_3]^{5-}$, the preferred proportions of thiosulfate salt to silver salt are equal to or greater than 2 moles of thiosulfate salt for 1 mole of silver salt. The most preferred proportions of thiosulfate salt to silver salt are equal to or greater than 3-to-1.

In making the aqueous solution of the silver thiosulfate ion complexes, the preferred silver halide is silver chloride. It should be noted that the silver chloride, as well as other silver halides, can be made in situ in the aqueous solution. In this way, a water-soluble silver salt such as silver nitrate or silver acetate is first dissolved in the aqueous solution. An equivalent or greater molar amount of a halide salt containing the chloride ion, such as sodium chloride, potassium chloride, and the like, is then added, resulting in the precipitation of the silver chloride salt.

Additionally, in making the aqueous solution of the silver thiosulfate ion complexes, it is preferred that the concentration of the initial silver halide in the aqueous solution be less than 25%. Higher concentrations of the silver halide can lead to instability of the resulting silver thiosulfate solution; that is to say, the silver thiosulfate ion complexes within the solution will "break down" or decompose, leading to discoloration of the solution and precipitation of silver sulfide.

The second step in the process entails the addition of a solvent to the aqueous solution resulting from the first step to create a biphasic separation; in this way, the silver thiosulfate ion complexes separate into one phase. The preferred solvents are those which are water miscible. Solvents such as ethyl alcohol, isopropyl alcohol, methyl alcohol, acetone, tetrahydrofuran, and the like, are examples of solvents which are useful in causing phase separation. The solvent is added to the silver thiosulfate ion complexes solution in an amount such that the solution separates into two phases. During the formation of two distinct phases, the silver thiosulfate ion complexes separate into one phase. Typically, the volume of the phase containing the silver thiosulfate ion complexes is only a fraction (e.g., less than 20%) of the total volume of liquid; this denser liquid phase resembles a liquid mixture containing a heavy oil and an aqueous solution where the heavy oil accumulates at the bottom of the vessel containing the liquid mixture.

The phase containing the silver thiosulfate ion complexes is thought to consist of a high concentration (i.e., 50–70% of the total volume) of relatively pure silver thiosulfate ion complexes and water. Excess thiosulfate salts, waste salts, solvent, and other contaminants are thought to remain in the other (larger) phase of the biphasic solution.

In the third step, the separated phase containing the silver thiosulfate ion complexes can be collected using well known means. For example, the phase can be drawn up using a pipet and removed from the solution. Likewise, a separatory funnel can be used to separate the phase from the solution.

After the liquid phase containing the silver thiosulfate ion complexes has been collected, the fourth step involves treatment of the collected phase to create essentially anhydrous silver thiosulfate complexes. The silver thiosulfate complexes are purified, containing insignificant amounts of waste salts (e.g., sodium nitrate or sodium acetate) and other extraneous materials. Treatments which are useful include, but are not limited to, evaporation, oven drying, freeze drying, solvent extraction, and the like. After the treatment, the essentially anhydrous silver thiosulfate complexes are ground into a fine powder.

B. Process for Producing Silver Thiosulfate Ion Complexes When the Ratio of Thiosulfate Ions to Silver Ions is Less Than 2-to-1

The process for producing essentially anhydrous silver thiosulfate ion complexes when the ratio of thiosulfate ions to silver ions is less than 2-to-1 involves four major steps. The first step, making an aqueous solution of silver thiosulfate ion complexes, is analogous to the first step of the process where the ratio is greater than 2-to-1. The major difference of this process from that where the ratio is greater than 2-to-1 is that the second step of this process involves precipitation of the silver thiosulfate ion complexes from the aqueous solution (described below).

In the second step, a solvent is added to the aqueous solution of silver thiosulfate ion complexes to precipitate the silver thiosulfate ion complexes. The preferred solvents are those solvents which are water miscible. Solvents such as ethyl alcohol, isopropyl alcohol, methyl alcohol, acetone, tetrahydrofuran, etc., are examples of solvents which are useful in causing precipitation. The solvent is added to the silver thiosulfate ion complexes solution in an amount such that the complexes precipitate.

In the third step, the silver thiosulfate ion complexes precipitate can be separated from the solution using any standard, well-known technique. Filtration represents one preferred separation technique. The silver thiosulfate ion complexes are relatively pure, containing insignificant amounts of waste salts (e.g., sodium nitrate or sodium acetate) and other extraneous materials like excess thiosulfate salts that are thought to remain in solution (i.e., they do not form a solid precipitate).

Following separation, the fourth and final step of removing essentially all remnant water from the complexes from the collected phase creates essentially anhydrous silver thiosulfate ion complexes. Methods which are useful include, but are not limited to, evaporation, oven drying, freeze drying, and the like. After the treatment, the essentially anhydrous silver thiosulfate ion complexes are ground into a fine powder.

C. The Nature of the Silver Thiosulfate Ion Complexes

While the benefit provided by the complexes of the present invention is not limited by an understanding of the precise nature of the complexes, the solid material produced by the two processes described above is thought to consist of a salt where the silver thiosulfate ion complexes are represented by the formulas $[Ag(S_2O_3)_2]^{3-}$, $[Ag(S_2O_3)_3]^{5-}$, $[Ag_2(S_2O_3)_3]^{4-}$, $[Ag_3(S_2O_3)_4]^{5-}$, and similar complexes. Unexpectedly, it was found that the form of the silver thiosulfate ion complexes produced is very dependent on the ratio of thiosulfate ion to silver ion.

If the ratio of the thiosulfate ion to silver ion is low (i.e., less than 2:1), silver thiosulfate ion complexes represented by the formulas $[Ag_2(S_2O_3)_3]^{4-}$, $[Ag_3(S_2O_3)_4]^{5-}$ and the like can be produced. The preferred silver thiosulfate ion complexes are those represented by $[Ag_2(S_2O_3)_3]^{4-}$, which can be produced in accordance with the following chemical equation:

Conversely, if the ratio of the thiosulfate ion to silver ion is high (i.e., greater than 2:1), relatively pure silver thiosulfate ion complexes represented by the formulas $[Ag(S_2O_3)_2]^{3-}$, $[Ag(S_2O_3)_3]^{5-}$ and the like can be produced.

The preferred silver thiosulfate ion complexes are those produced when the ratio of the thiosulfate ion to silver ion is low. The purified silver thiosulfate ion complexes are carrier-free, photostable, highly water soluble, non-staining and antimicrobially active. This combination of features is not present in any commercially available or previously described silver-containing composition.

II. Compositions Containing Silver Thiosulfate Ion Complexes

Topical antimicrobial agents include therapeutic heavy metal compounds such as silver-containing compounds. Silver, in its ionic state ($Ag^+$), possesses a broad spectrum of antibacterial, antifungal, and antiviral properties and is relatively safe. Early studies showed that the silver ion is oligodynamic, i.e., active at very low concentrations. [See generally, Russell et al., Antimicrobial Activity and Action of Silver," Progress in Medicinal Chemistry 31:351–70 (1994)].

The present invention is directed at, among other things, carrier-free silver thiosulfate ion complexes compositions.

The provision of carrier-free silver thiosulfate ion complexes is advantageous for at least two reasons. First, it provides the ability to make antimicrobial silver thiosulfate ion complexes compositions without the need for potentially irritating porous carrier particles. Second, it provides the ability to produce antimicrobial silver thiosulfate ion complexes compositions which can contain high concentrations of silver, resulting in compositions with potent antimicrobial activity.

As set forth above, the carrier-free silver thiosulfate ion complexes are stable. However, the complexes are not stable in all pharmaceutically-acceptable compositions. Indeed, it was found that the silver thiosulfate ion complexes decompose when incorporated into certain base compositions (See Experimental Section, infra). The decomposition of the silver thiosulfate ion complexes results in the silver-based composition both changing to a black color and losing antimicrobial activity. Given the instability of silver thiosulfate ion complexes when incorporated in certain base compositions, it was surprising and unexpected to discover silver thiosulfate ion complexes compositions which were, in fact, stable.

The stable silver thiosulfate ion complexes compositions of the present invention comprise carrier-free suspended silver thiosulfate ion complexes in a base. The preferred base is anhydrous, and in one embodiment the base is semisolid. The stable silver-based compositions maintain their antimicrobial activity. Moreover, the amount of silver in the compositions can be varied over a large range of concentrations to provide compositions with different levels of antimicrobial potency.

During the first step of the previously-described process for producing essentially anhydrous silver thiosulfate ion complexes, an aqueous solution of the complexes is made. It should be noted that aqueous solutions of silver thiosulfate ion complexes can be added to an ointment or cream base to make an antimicrobial ointment or cream composition; in other words, a composition can be made after completing only the first of the four steps. However, the resulting antimicrobial ointment or cream composition suffers from two major drawbacks. First, the resulting silver thiosulfate ion complexes compositions will contain large quantities of excess thiosulfate salts as well as waste salts (e.g., sodium nitrate, potassium nitrate, and potassium acetate). When applied topically, the antimicrobial composition containing these impurities may be irritating. The second major problem is that ointment or cream compositions made with silver thiosulfate ion complexes from such an aqueous solution are not stable for long periods of time. That is to say, over a period of time the resulting silver-based antimicrobial compositions will turn black and lose antimicrobial efficacy.

This destabilization occurs whether or not the silver-based compositions are stored in an opaque container or a clear container. Therefore, the destabilization is not a photo-reduction of the silver. Rather, what occurs is that the thiosulfate ion component of the silver thiosulfate ion complexes experiences a chemical breakdown. The effect of this chemical process is the breakdown of the silver thiosulfate ion complexes.

Again, while an understanding of the mechanisms involved is not necessary, it is believed that the thiosulfate ion which makes up the silver thiosulfate ion complexes is formed by adding a sulfur atom to a sulfite ion in a complex reaction that can be summarized by the following chemical equation: $S + SO_3^{2-} \rightarrow S_2O_3^{2-}$. The sulfur atom that is added to the sulfite ion to give $S_2O_3^{2-}$ is somewhat labile; thus, $S_2O_3^{2-}$ may appropriately be represented as $S-SO_3^{2-}$. In aqueous solutions, thiosulfate decomposes over time. At moderately low pH levels the sulfur atom readily splits off, nominally yielding sulfur as follows:

$$S-SO_3^{2-} + H^+ \rightarrow S + HSO_3^{1-}$$

While the acid decomposition of the thiosulfate ion nominally yields sulfur, it should be mentioned that very finely divided particles of sulfur in an acidic aqueous solution have the character of polysulfide ions. [Levenson: Complementary Processes (Ch. 14), in *The Theory of the Photographic Process*, Fourth Ed. MacMillan Publishing Co., Inc., New York (1977)].

As a result of the instability of the thiosulfate ion, when dissolved in water silver thiosulfate ion complexes also chemically decompose over time. It is believed that when the thiosulfate component of the silver thiosulfate ion complexes chemically breaks down, it releases silver ions which react with the released sulfur ions to form silver sulfide. Silver sulfide is a black material having the molecular formula of $Ag_2S$. Due to silver sulfide's high dissociation constant (pK=49.1), silver sulfide is essentially non-antimicrobial. That is to say, the silver ion is bound tightly to the sulfur ion so that it can only ionize very slowly from the silver sulfide salt. As a result, little, if any, ionized silver is available to provide antimicrobial activity.

Likewise, silver thiosulfate ion complexes, when added to either an ointment base which contains a small proportion of water or a water-containing cream base in order to form an antimicrobial composition, will decompose over a relatively short period of time. The resulting antimicrobial composition will turn black as the silver thiosulfate ion complexes in the composition decompose to silver sulfide. Additionally, the composition will lose its antimicrobial efficacy with decomposition of the silver thiosulfate ion complexes.

In contrast, the previously described four-step process for producing essentially anhydrous silver thiosulfate ion complexes allows the production of compositions that are stable over long periods of time. The stable silver thiosulfate ion complexes compositions of this invention comprise carrier-free suspended silver thiosulfate ion complexes in a base. The bases which are most useful for the present invention entail any compound or mixture which is capable of suspending the complexes. Preferably, the base is essentially anhydrous and can be used topically to deliver a medicinal agent. By way of illustration, bases that are useful include white petrolatum, AQUAPHOR® (an ointment base comprising Petrolatum, Mineral Oil, Ceresin, and Lanolin Alcohol), polaxomers, and polyethylene glycol (PEG) polymers with molecular weights greater than 600. The preferred base is a PEG ointment composition containing a combination of PEG polymers with molecular weights greater than 1,000 and polaxomers.

The methods for suspending the purified silver thiosulfate ion complexes, in the form of a fine powder, into a base to form a silver-based antimicrobial composition are well known in the art. For example, one method involves heating the base until it has liquefied; then, while the base cools, adding the silver thiosulfate ion complexes and stirring until the base has resolidified. This method produces a suspension of the silver thiosulfate ion complexes within the base, preferably a homogeneous suspension.

The concentration of the silver thiosulfate ion complexes within the base is such as to provide antimicrobial activity. The preferred concentration of the silver thiosulfate ion complexes is 0.1% to 3.0%. However, silver thiosulfate ion complexes concentrations can range up to 10% to 30% depending on the antimicrobial potency required. The most preferred concentration is between 0.2% and 1.5%. Generally speaking, the effective concentration is that concentration which is higher than the minimum inhibitory concentration for a particular microbe. As would be expected, certain microbes are more sensitive to silver than other microbes, e.g., gram (−) microbes are generally more sensitive than gram (+) microbes. As a result, a concentration less than 0.1% could be effective depending on the microbe and the intended use of the final product.

The resulting silver thiosulfate ion complexes compositions of the present invention are antimicrobially active and stable when compared to compositions that use bases which are not anhydrous. Additionally, the silver-based antimicrobial compositions of this invention show no photo-discoloration when exposed to ambient room light over a 72 hour period.

Though the compositions must be in an anhydrous base in order to maintain their stability, it is not intended that the compositions of the present invention be limited by the particular nature of the therapeutic preparation. For example, the present invention contemplates compositions that include physiologically tolerable diluents, adjuvants and excipients, such as pharmaceutical grades of mannitol, lactose, starch, magnesium stearate, sodium saccharin, cellulose, magnesium carbonate, and the like. These compositions typically contain 1%–95% of active ingredient, preferably 2%–70%. In addition, if desired the compositions may contain minor amounts of auxiliary substances such as stabilizing or pH buffering agents or preservatives.

III. Therapeutic Use of Compositions Containing Silver Thiosulfate Ion Complexes The silver thiosulfate ion complexes compositions of the present invention can be used topically, for example, on skin, in wounds, in the eyes, nose, and mouth, in the treatment and prevention of infection. As alluded to above, the compositions are effective against bacteria, viruses, and fungi. For example, *E. coli* and many species of Klebsiella, Proteus, Pseudomonas, Staphylococcus, and Candida may be inhibited or killed by the compositions of the present invention. In general, the dosage required for therapeutic efficacy will vary according to the microbe involved, the type of use and mode of administration, as well as the particularized requirements of individual hosts.

The therapeutic preparations can be administered for clinical use in humans and for veterinary use, such as with domestic animals, in manners known in the art and similar to other therapeutic agents. Though not limited to any particular means of application, the antimicrobial compositions can be applied using gloved hands or by an applicator. Likewise, the antimicrobial compositions can be applied to the surface of a dressing, which can then be applied topically. Ophthalmic infections can be treated using standard procedures in the art, such as by pulling down the lower eyelid to form a pocket and applying the composition thereto. By way of further illustration, infections of the mouth can be treated by applying the composition with a sponge applicator or a toothbrush.

Bacterial resistance to silver is known to occur in certain situations; more specifically, *Escherichia coli* and *Salmonella typhimurium* are known to develop plasmid-encoded plasmid-encoded resistance to silver. [Russell et al., Progress in Medicinal Chemistry 31:351–70 (1994)]. Two related methods are commonly used to prevent and combat drug resistance.

The first method entails the combination of two or more therapeutic agents into a final composition. For example, the β-lactamase inhibitor clavulanate potassium has been added to amoxicillin, resulting in a combination preparation (Augmentin™; SmithKline Beecham) with expanded antimicrobial activity. While clavulanic acid has only weak antibacterial activity when used alone, its combination with amoxicillin results in a synergistic effect.

The second method entails the concomitant administration of two or more distinct antimicrobial agents. This method is based on the principle that a microbe that is resistant to one agent may be susceptible to another. This is especially important, e.g., in tuberculosis, which is caused by *Mycobacterium tuberculosis*. Particular *M. tuberculosis* bacteria that cause tuberculosis are known to display resistant to each of the primary therapeutic agents. As a result, treatment of tuberculosis often requires combinations of three or more drugs for periods exceeding one year. [See Dooly et al. "Multidrug-resistant tuberculosis," Ann. Int. Med. 117:257–59 (1992); Nadler "Multidrug resistant tuberculosis," N. Eng. J. Med. 327:1172–75 (1992)].

The present invention contemplates combining a topical silver-containing preparation with another medicinal agent to form a pharmaceutical composition. Indeed, the present invention contemplates the use of many diverse medicinal agents, including antimicrobial agents, topically active drugs, and systemically active drugs. The preferred medicinal agents contemplated for use in the pharmaceutical compositions of the present invention are those that can be used as antimicrobial agents in the treatment and prevention of infection and disease. Suitable antimicrobial agents include, but are not limited to, penicillin, tetracycline, oxytetracycline, chlortetracycline, chloramphenicol, chlorhexidine, mupirocin, metronidazole, miconazole, acyclovir, itraconazole and sulfonamides. Additional antimicrobial agents include antimicrobial peptides such as magainins, cecropins, protegrins, bacteriocins and defensins.

The pharmaceutical compositions of the present invention possess an additional broad spectrum of antimicrobial protection by combining antimicrobial medicinal agents in a stable fashion with silver thiosulfate ion complexes. Furthermore, as previously indicated, the use of silver thiosulfate ion complexes with an antimicrobial medicinal agent may aid in preventing the formation of drug-resistant microbes. Moreover, since silver ions are oligodynamic and are riot immediately exhausted (i.e., they have a long-lasting or "residual" effect), the presence of silver ions in the pharmaceutical compositions results in compositions which are longer lasting than those containing a single antimicrobial agent.

Medicinal agents besides antimicrobial agents are also contemplated for use in the pharmaceutical compositions of the present invention, including topically active drugs for the treatment of diseases. Suitable topically active drugs include, but are not limited to, acne preparations such as isotretinoin, benzoyl peroxide, salicylic acid and tetracycline; anesthetics for topical administration such as dibucaine, lidocaine, benzocaine, tetracaine, deperodon and pramoxine hydrochloride; anti-inflammatory agents such as betamethasone benzoate, betamethasone valerate, desonide, fluocinolone acetonide, halcinonide, hydrocortisone; antiperspirants and medications used in the treatment of hyperhidrosis such as glutaraldehyde, methenamine, glycopyrrolate, scopolamine hydrobromide; antipruritic and external analgesic agents such as camphor, menthol, salicylic acid, methylsalicylate; cleansing agents such as soaps and shampoos; keratolytic, cytotoxic, and destructive agents such as anthralin, cantharidin, fluorouracil, podophyllotoxin, resorcinol; and pigmenting and depigmenting agents, sunscreens such as hydroquinone, monobenzone, trioxsalen and p-aminobenzoic acid; anabolic steroids for building up tissues under wound healing such as methandienone; proteolytic agents for the decomposition of fibrin such as trypsin; vasodilating substances for improving the flow of blow during wound healing such as tolazoline; thrombosis-hampering substances such as heparin; certain biologically active substances which affect tissue formation and tissue stabilization such as ascorbic acid and EGF (epidermal growth factor), EGF-URo (EGF-urogastron), somatostatin, somatotropin asellacrine, and TGF; and mucolytic and antiviral medicaments which are globulins such as lysozyme.

A pharmaceutical composition with a broad spectrum of antimicrobial protection is produced by combining one or more topically active drugs in a stable fashion with a pharmaceutical composition containing silver thiosulfate ion complexes. In situations where the topically active drugs are used to treat a disease which has an abundance of dead tissue (e.g., a fungating tumor or a decubitus ulcer), the addition of antimicrobial silver ions will aid in the prevention of a secondary infection at the diseased site. Furthermore, the presence of ionized silver in the pharmaceutical composition can aid in the prevention of malodor caused by anaerobic and aerobic microbes at the diseased site. Finally, combining a topically active drug with the silver thiosulfate ion complexes minimizes the need to apply additional topical antimicrobial compositions which may be incompatible with the medicinal agent, resulting in both time and cost savings.

In addition to medicinal agents which are antimicrobial agents or topically active agents, the present invention also contemplates the use of systemically active drugs in the pharmaceutical compositions of the present invention. The systemically active drugs are absorbed by the body surface when applied topically, either neat or with the aid of a solvent. Suitable systemically active drugs include, but are not limited to, sedatives and hypnotics such as pentobarbital sodium, phenobarbital, secobarbital sodium, carbromal, and sodium phenobarbital; psychic energizers such as 3-(2-1-aminopropyl)-indole acetate and 3-(2-aminobutyl)-indole acetate; tranquilizers such as reserpine, chlorpromazine hydrochloride, and thiopropazate hydrochloride; hormones such as adrenocorticosteroids, for example, 6-α-methylprednisolone, cortisone, cortisol, and triamcinolone; androgenic steroids, for example, methyl-testosterone, and fluoxymesterone; estrogenic steroids, for example, estrone, 17β-estradiol and ethinyl estradiol; progestational steroids, for example 17-α-hydroxyprogesterone acetate, medroxyprogesterone acetate, 19-norprogesterone, and norethindrone; and thyroxine; antipyretics such as aspirin, salicylamide, and sodium salicylate; antispasmodics such as atropine, methscopolamine bromide, and methscopolamine bromide with phenobarbital; antimalarials such as the 4-aminoquinolines, 8-aminoguinolines, and pyrimethamine; and nutritional agents such as vitamins, essential amino acids, and essential fats.

A pharmaceutical composition with a broad spectrum of antimicrobial protection is produced by combining one or more systemically active drugs in a stable fashion with silver thiosulfate ion complexes. The addition of silver thiosulfate ion complexes with one or more systemically active drugs to produce a pharmaceutical composition assists in the preservation of the pharmaceutical composition by protecting it from microbial proliferation and overgrowth, which could otherwise lead to spoilage of the medicinal composition containing the systemically active drugs.

Finally, the antimicrobial compositions may be useful in making infection-resistant cosmetics and personal care products.

IV. Incorporation of Silver Thiosulfate Ion Complexes into Matrices and the Use of Such Matrices This section describes the incorporation of silver thiosulfate ion complexes into matrices, most preferably anhydrous polymeric matrices. In turn, the matrices products can be used in conjunction with medical devices for the treatment and prevention of infections and diseases. In general, the silver thiosulfate ion complexes can be incorporated into the polymer matrix either (i) during the production of the polymer matrix or (ii) after the polymer matrix has been produced. It is most preferred that the complexes are homogeneously dispersed in the matrix.

A. The Nature of Silver Thiosulfate Ion-Containing Anhydrous Polymeric Matrices

Similar to the situation described above regarding compositions, aqueous solutions of silver thiosulfate ion complexes which have not been purified can be incorporated into polymer matrices to render the matrices compositions antimicrobial. However, the resulting matrices compositions will contain large quantities of excess thiosulfate salts as well as waste salts such as sodium nitrate, potassium nitrate, potassium acetate, etc. As set forth above, these impurities may be irritating when the matrices compositions are applied topically. Furthermore, the presence of the waste salts may have a negative impact on the physical characteristics (e.g, feel, strength, and stiffness) of the final matrices compositions.

The purified carrier-free silver thiosulfate ion complexes of this invention can be incorporated into an anhydrous polymer matrix to produce photostable antimicrobial matrices compositions; these compositions are useful in making medical devices. The present invention contemplates that any solid material that does not contain a significant amount of water may be used as an anhydrous polymer matrix. The preferred anhydrous polymer matrix material is any material that is compatible (i.e., does not contain reactive components which could lead to the destruction of the thiosulfate ligand, thereby destabilizing the silver thiosulfate ion complexes) with the silver thiosulfate ion complexes of this invention. The most preferred polymer matrix material is one that is compatible with the silver thiosulfate ion complexes of this invention and has some capacity to absorb and/or swell in the presence of water; the ability of the polymer matrix to absorb and/or swell in the presence of water assists in the dissolution and diffusion of the silver thiosulfate ion complexes from the polymer matrix.

It should be noted that the silver thiosulfate ion complexes of the present invention can be used with anhydrous polymer matrices which do have reactive components as long as the media is such that the reactive chemical component of the polymer matrices cannot react with the silver thiosulfate ion complexes. For example, when incorporated into a solution of alginate material (which contains a number of chemical reactive groups such as carboxylic acid), the silver thiosulfate ion complexes of the resulting composition are unstable over long periods; the water in the solution acts as a media in which the reactive groups of the alginate materials can destabilize the silver thiosulfate ion complexes. However, when the alginate material is dry, the silver thiosulfate ion complexes remain stable.

Anhydrous polymer matrix materials useful in this invention include, but are not limited to, the following: adhesives such as acrylic-based, pressure-sensitive adhesives; biopolymers such as silk, alginate materials, etc.; hydrocolloid materials such as sodium carboxymethylcellulose, either alone or when bound in a polymer; polymers such as polyurethane, silicone, etc. in the form of coatings, films or foams, and the like. These anhydrous polymer matrix compositions can be used alone or as a component of another material, such as a medical device.

The concentration of the silver thiosulfate ion complexes within the anhydrous polymeric matrix should be such as to provide antimicrobial activity. The preferred concentration of the silver thiosulfate ion complexes in the final polymeric matrix is 0.1% to 3.0%. However, silver thiosulfate ion complexes concentrations can range up to 10% to 30%, depending on the antimicrobial potency required and the permeability of the polymeric matrix. The most preferred concentration is between 0.2% and 1.5%. The resulting silver thiosulfate ion complexes-containing matrices compositions of this invention are antimicrobially active and stable. Additionally, the compositions of this invention show no photo-discoloration when exposed to ambient room light over a 72-hour period.

It should be noted that the silver thiosulfate ion complexes-containing matrices compositions of the present invention can be used alone in the treatment and prevention of infection in a manner analogous to the compositions described above. Moreover, as previously alluded to, the matrices compositions can be used to make medical devices such as dressings, tamponades, etc. which can be used in the treatment and prevention of infection.

B. Incorporation During Production of Polymer Matrix

The method of incorporating the silver thiosulfate ion complexes during the production of the polymer matrix itself will be dependent on the production process for that polymer matrix. The methods of incorporation for several polymer matrices follows. Of course, deviations from these methods as well as the use of different matrices than those specifically mentioned are within the scope of the present invention.

The first method of incorporation is useful if the polymer matrix is produced from a solvent solution of polymer matrix material. In this situation, the silver thiosulfate ion complexes in a solid powder form can be added to that solution and mixed thoroughly. Upon elimination of the solvent through standard means in the art, the remaining polymer matrix material will have the silver thiosulfate ion complexes dispersed; preferably the complexes are dispersed homogeneously. For example, in an adhesive material dissolved in a solvent, the silver thiosulfate ion complexes in a powder form are thoroughly mixed in. The mixture is then coated on a liner and dried. The resulting adhesive film has the silver thiosulfate ion complexes incorporated as a dispersion.

Another method of incorporation is useful if the production process for the polymer matrix involves the use of water as a solvent, (i.e., latex polymer systems, solvent extraction systems) or as a reactant (i.e., polyurethane foam production, alginate fiber production, etc.). With this method, the silver thiosulfate ion complexes can be dissolved in the water prior to the production process. To illustrate, if a polymer film is being produced by coating with a polymer latex solution, the silver thiosulfate ion complexes can be added directly to the latex solution. Once added, the silver thiosulfate ion complexes will dissolve. After coating and drying, the resulting polymer film will have the silver thiosulfate ion complexes homogeneously dispersed in the film.

Likewise, in producing a polyurethane foam matrix by reacting the polyurethane prepolymer with water, the silver thiosulfate ion complexes can be dissolved in the water prior to reacting it with the prepolymer. After the polyurethane foam has reacted and been dried, the silver thiosulfate ion complexes will be dispersed throughout the foam matrix.

Additionally, in producing a water insoluble alginate material by reacting an alginate solution with an aqueous calcium chloride bath, the silver thiosulfate ion complexes can be dissolved in either the water making up the alginate solution or the calcium chloride bath. The alginate solution, when extruded into the calcium chloride bath, will result in crosslinked alginate fibers which incorporate the silver thiosulfate ion complexes. Upon drying of these fibers, the silver thiosulfate ion complexes will be dispersed throughout the alginate matrix.

Another method of incorporation can be used in conjunction with the production of polymer matrices such as a hydrocolloid matrix made up of a hydrocolloid material (e.g., carboxymethylcellulose) in a polymer binder. In this situation, the silver thiosulfate ion complexes, in a solid form, can be mixed directly with the hydrocolloid material prior to the production process. Likewise, the silver thiosulfate ion complexes can be dissolved in water which is then used to treat the hydrocolloid material so that the solution is absorbed by the hydrocolloid material and then dried. Thereafter, the treated hydrocolloid material is processed using standard procedures to produce the hydrocolloid polymer matrix which contains the silver thiosulfate ion complexes dispersed in the hydrocolloid component of the matrix.

C. Incorporation After Production of Polymer Matrix

In addition to incorporation prior to or during the production of the polymer matrix, silver thiosulfate ion complexes can be incorporated after the polymer matrix has been produced. One approach is to form an aqueous solution of the silver thiosulfate ion complexes and then apply this solution to the finished polymer matrix. This silver thiosulfate ion complexes solution can be applied to the polymer matrix by spraying, dipping, painting or other suitable means.

By way of illustration, an aliquot of the silver thiosulfate ion complexes can be applied onto and absorbed into a finished foam dressing. After drying, the silver-based foam composition will be stable and antimicrobial. Likewise, the silver thiosulfate ion complexes solution can be sprayed on the surface of a polymer or adhesive film which, after drying, will be stable and antimicrobial.

D. Precautions During Incorporation

Regardless of the method of incorporating the silver thiosulfate ion complexes with the polymeric matrix, certain precautions need to be considered. First, if incorporation of the silver thiosulfate ion complexes into the polymeric matrix involves the use of water, it is very important that the water be removed from the polymeric matrix. If the water is not removed, the silver thiosulfate ion complexes will become destabilized within the polymeric matrix over time.

Second, though the water can be removed using any standard method, if the water is removed by drying the polymeric matrix in an oven, care should be taken to use only moderate temperatures; temperatures of 20° C. to 70° C. may be used, while temperatures of 30° C. to 50° C. are preferred. If the temperature becomes too hot, rapid destabilization of the silver thiosulfate ion complexes can occur.

Finally, when the silver thiosulfate ion complexes are in solution, contact with metal surfaces should be avoided. The silver thiosulfate ion complexes solution can be destabilized upon contact with metal surfaces such as aluminum and copper. An effort should be made to ensure that the solution comes into contact with materials such as glass or plastic, which appear to be less destabilizing.

EXPERIMENTAL

In the disclosure which follows, the following abbreviations apply: L (liters); ml (milliliters); µl (microliters); g (grams); mg (milligrams); µg (micrograms); mol (moles); mmol (millimoles); µmol (micromoles); cm (centimeters); mm (millimeters); nm (nanometers); °C. (degrees Centigrade); MW and M.W. (molecular weight); N (normal); w/w (weight-to-weight); w/v (weight-to-volume); min. (minutes); No. (number); ICP (inductively coupled plasma); CFU (colony forming units); PEG (polyethylene glycol); MHM (Mueller Hinton Medium); ZOI (zone of inhibition); ATCC (American Type Culture Collection, Rockville, Md.); USP (United States Pharmacopeia); NCCLS (National Committee for Clinical Laboratory Standards); NIOSH (National Institute of Safety and Health); Avitar (Avitar, Inc., Canton, Mass.); Aldrich (Milwaukee, Wis.); Avery Dennison, Inc. (Mill Hall, Pa.); BASF (BASF Corp., Chemical Division; Parsippany, N.J.); Belersdorf Inc. (BDF Plaza Norwalk, Conn.); Columbus (Columbus Chemical Industries; Columbus, Wis.); Cook Composites and Polymers (Kansas City, Mo.); Difco (Difco Laboratories, Detroit, Mich.); Hampshire (Hampshire Chemical Co., Lexington, Mass.); Johnson & Johnson Medical, Inc. (Arlington, Tex.); Owen Laboratories (San Antonio, Tex.); Protan (Drammen, Norway); Roundy (Roundy's Inc., Milwaukee, Wis.); Sigma (Sigma Chemical Company, St. Louis, Mo.); SmithKline Beecham (Philadelphia, Pa.); Steriseal (Steriseal Ltd, England); Whatman (Whatman International Ltd., England); WOHL (Wisconsin Occupational Health Laboratory, Madison, Wis.).

The following examples serve to illustrate certain preferred embodiments and aspects of the present invention and are not to be construed as limiting the scope thereof. The experimental disclosure which follows is divided into: I) Processes To Obtain Silver Thiosulfate Ion Complexes; II) Compositions Containing Silver Thiosulfate Ion Complexes; III) Antimicrobial Activity Of Compositions Containing Silver Thiosulfate Ion Complexes; IV) Use Of Silver Thiosulfate Ion Complexes in Medical Devices, and V) Use Of Silver Thiosulfate Ion Complexes in Combination With Other Medicinal Agents.

I. Processes to Obtain Silver Thiosulfate Ion Complexes

EXAMPLE 1
Process for Making Silver Thiosulfate Ion Complexes Using Silver Chloride When the Ratio of Thiosulfate Ions to Silver Ions is Greater Than 2-to-1

This example illustrates the process for producing silver thiosulfate ion complexes when the ratio of thiosulfate ions to silver ions is greater than 2-to-1. That is, a biphasic separation is employed in this example.

The silver thiosulfate ion complexes were produced by first making a silver chloride precipitate in an aqueous solution (hereafter, "silver chloride precipitate/aqueous solution"). The silver chloride precipitate/aqueous solution was made by mixing 20 ml of a silver nitrate (Aldrich; deionized water as the diluent) solution (1 mmol/ml) with 22 ml of a sodium chloride solution (1 mmol/ml) (Aldrich; deionized water as the diluent) in a 500 ml separatory funnel. To the resulting silver chloride precipitate/aqueous solution was added 60 ml of a sodium thiosulfate (Columbus; deionized water as the diluent) solution (1 mmol/ml). The resulting mixture was agitated by shaking the separatory funnel until all of the silver chloride precipitate was dissolved.

The silver thiosulfate ion complexes produced were separated by adding 200 ml of ethyl alcohol to the container. Upon addition of the ethyl alcohol, the solution became cloudy and separated into two separate phases. The two phases were separated using the separatory funnel. The weight of the material in the phase containing the silver thiosulfate ion complexes was approximately 17 g. This phase was then treated by adding 70 ml ethyl alcohol and 40 ml of acetone to make the silver thiosulfate ion complexes essentially anhydrous. After sitting overnight, the silver thiosulfate ion complexes were in the form of a pure, white solid material in the bottom of the container. Thereafter, the solvent was decanted and the white solid was dried in an oven (62° C.) and ground to a fine white powder using a mortar and pestle. The weight of the dried silver thiosulfate ion complexes was 10.03 g.

The silver thiosulfate ion complexes were analyzed for silver, sodium and sulfur using Inductively Coupled Plasma Argon Emission Spectrometry. The analysis, performed by Wisconsin Occupational Health Laboratory (WOHL), included measurement of the amount of silver using a method based on NIOSH SI182. Briefly, a representative portion of the silver thiosulfate ion complexes was weighted and diluted 1/1000 in a dilute nitric acid solution. Thereafter, an aliquot of the sample was analyzed (Jarrel ASH ICP; Franklin, Mass.); the analysis gave the following results (expressed as percentages of the air dried samples):

Silver 20%

Sodium 17%

Sulfur 32%

The results of the analysis suggest that the silver thiosulfate ion complexes were relatively pure and corresponded to the formula: $Na_4H[Ag(S_2O_3)_3]$ (Silver: 20.11% (w/w), Sodium: 17.13% (w/w), Sulfur: 35.75% (w/w)).

The calculated yield of silver thiosulfate ion complexes using the process of this example is 93.7%.

EXAMPLE 2
Process For Making Silver Thiosulfate Ion Complexes Using Silver Chloride When The Ratio Of Thiosulfate Ions To Silver Ions Is Equal To 2-to-1

This example illustrates the process for producing silver thiosulfate ion complexes when the ratio of thiosulfate ions to silver ions is equal to 2-to-1. The silver thiosulfate ion complexes were isolated through the use of a biphasic separation.

In this example, silver thiosulfate ion complexes were produced by first making a silver chloride precipitate in an aqueous solution by mixing 10 ml of a silver nitrate (Aldrich; deionized water as the diluent) solution (1 mmol/ml) with 10 ml of a sodium chloride (Aldrich; deionized water as the diluent) solution (1 mmol/ml) in a 100 ml specimen container. To this silver chloride precipitate/aqueous solution was added 20 ml of a sodium thiosulfate (Columbus; deionized water as the diluent) solution (1 mmol/ml). The resulting mixture was agitated by shaking the container until all of the silver chloride precipitate was dissolved.

Thereafter, the silver thiosulfate ion complexes were separated by adding 50 ml of acetone to the container. Upon addition of the acetone, the solution became cloudy and separated into two separate phases. The two phases were separated into individual containers using a pipet. The phase containing the silver thiosulfate ion complexes was treated by adding 50 ml of acetone to make the silver thiosulfate ion complexes essentially anhydrous.

After sitting overnight, the silver thiosulfate ion complexes were in the form of a pure white solid material. Thereafter, the solvent was decanted and the white solid was dried in an oven (62° C.) and ground to a fine white powder using a mortar and pestle. The weight of the dried silver thiosulfate ion complexes was 3.97 grams.

The resulting silver thiosulfate ion complexes material was analyzed for silver, sodium and sulfur using an Inductively Coupled Plasma (ICP; described above). The analysis gave the following results:

Silver 25%

Sodium 17%

Sulfur 30%

The results of the analysis indicate that the silver thiosulfate ion complexes were relatively pure corresponding with the following theoretical formula: $Na_3[Ag(S_2O_3)_2]$ $.2H_2O$. (Silver: 24.7% (w/w), Sodium: 15.78% (w/w), Sulfur: 29.3% (w/w)).

The calculated yield of making silver thiosulfate ion complexes using the process of this invention is 90.8%.

EXAMPLE 3
Process For Making Silver Thiosulfate Ion Complexes Using Silver Chloride When The Ratio Of Thiosulfate Ions To Silver Ions Is Less Than 2-to-1

This example further illustrates the process for producing silver thiosulfate ion complexes when the ratio of thiosulfate ions to silver ions is less than 2-to-1. As in the preceding example, the silver thiosulfate ion complexes were isolated through the formation of a precipitate rather than a biphasic separation.

In this example, silver thiosulfate ion complexes were made by first making a silver chloride precipitate in an aqueous solution by mixing 10 ml of a silver nitrate (Aldrich; deionized water as the diluent) solution (1 mmol/ml) with 20 ml of a sodium chloride (Aldrich; deionized water as the diluent) solution (1 mmol/ml) in a 100 ml specimen container. To this silver chloride precipitate/aqueous solution was added 15 ml of a sodium thiosulfate (Columbus; deionized water as the diluent) solution (1 mmol/ml). The resulting mixture was agitated by shaking the container until all of the silver chloride precipitate was dissolved.

Thereafter, the silver thiosulfate ion complexes were precipitated from the solution by adding 50 ml of acetone to the container. The precipitated silver thiosulfate ion complexes were in the form of a pure white solid material. The solvent was decanted and the white solid was dried in an oven (62° C.) and ground to a fine white powder using a mortar and pestle.

The silver thiosulfate ion complexes were analyzed for silver, sodium and sulfur using an Inductively Coupled Plasma (ICP; described above). The analysis gave the following results:

Silver 32%

Sodium 14%

Sulfur 29%

The results of the analysis indicate that the silver thiosulfate ion complexes were relatively pure corresponding with the following theoretical formula $Na_4[Ag_2(S_2O_3)_3]$ $H_2O$ (Silver: 32.6% (w/w), Sodium: 13.9% (w/w), Sulfur: 29.0% (w/w)).

EXAMPLE 4
Process for Making Silver Thiosulfate Ion Complexes Using Silver Bromide In making the aqueous solution of silver thiosulfate ion complexes, the preferred silver halide is silver chloride (Examples 1–3); this example illustrates that other silver halides may be used.

In this example, the silver thiosulfate ion complexes were produced by first making a silver bromide precipitate in an aqueous solution (hereafter, "silver bromide precipitate/aqueous solution") by mixing 2 ml of a silver nitrate (Aldrich; deionized water as the diluent) solution (1 mmol/ml) with 2.2 ml of a sodium bromide (Aldrich; deionized water as the diluent) solution (1 mmol/ml) in a 50 ml beaker. To this silver bromide precipitate/aqueous solution was added 6.0 ml of a sodium thiosulfate (Columbus; deionized water as the diluent) solution (1 mmol/ml). The resulting mixture was agitated by stirring until all of the sodium bromide precipitate was dissolved.

The silver thiosulfate ion complexes were separated by adding 20.0 ml of acetone to the container. Upon addition of the acetone, the solution separated into two phases. The phase containing the silver thiosulfate ion complexes was collected and treated by adding 7.0 ml ethyl alcohol and 4.0 ml of acetone to make the silver thiosulfate ion complexes anhydrous. After sitting overnight, the silver thiosulfate ion complexes were in the form of a white solid material at the bottom of the container. The solvent was decanted and the white solid was dried in an oven (62° C.) and ground to a fine white powder using a mortar and pestle. The resulting weight of the dried silver thiosulfate ion complexes was 0.88 g.

EXAMPLE 5
Process for Making Silver Thiosulfate Ion Complexes Devoid of a Phase Separation Procedure To illustrate the importance of making silver thiosulfate ion complexes using the processes of this invention, silver thiosulfate ion complexes were made by a process which did not use a phase separation procedure when the ratio of thiosulfate ions to silver ions is greater than 2-to-1.

This comparison process was performed by first making a silver chloride precipitate in an aqueous solution (hereafter, "silver chloride precipitate/aqueous solution") by mixing 2 ml of a silver nitrate (Aldrich; deionized water as the diluent) solution (1 mmol/ml) with 2.2 ml of a sodium chloride (Aldrich; deionized water as the diluent) solution (1 mmol/ml) in a 50 ml beaker. To this silver chloride precipitate/aqueous solution was added 6.0 ml of a sodium thiosulfate (Columbus; deionized water as the diluent) solution (1 mmol/ml). The resulting mixture was agitated by stirring until all of the sodium chloride precipitate was dissolved.

The resulting silver thiosulfate ion complexes solution was placed in a convection oven at 62° C. overnight to evaporate the water. The solid material produced had a splotchy tan color with areas which had a deep brown color. The lack of a pure white solid indicates that this process leads to a breakdown or decomposition of silver thiosulfate ion complexes.

II. Compositions Containing Silver Thiosulfate Ion Complexes

EXAMPLE 6
Stable Antimicrobial Composition—PEG Base

The previous examples were directed at processes for making silver thiosulfate ion complexes. This example, as well as Examples 7–9 that follow, compare various antimicrobial compositions containing the silver thiosulfate ion complexes. In this example, a silver-based antimicrobial composition was produced in a PEG base. Specifically, 40 g of a polyethylene glycol (PEG) base (PEG 600:PEG 1000= 0.3:0.7; Aldrich) was melted. While cooling, 0.47 g of the silver thiosulfate ion complexes of Example 1 were stirred into the melted PEG base. The stirring was continued until the silver thiosulfate ion complexes were homogeneously suspended. While stirring, the melted PEG/silver thiosulfate ion complexes composition was cooled to produce a semi-solid base. The amount of silver in this silver-based antimicrobial composition was equivalent to 0.5% silver nitrate.

EXAMPLE 7
Stable Antimicrobial Composition—AQUAPHOR®

To further illustrate a silver-based antimicrobial composition of this invention, 40 g of AQUAPHOR® Cholesterolized Absorbent Eurcerite Ointment Base was melted. AQUAPHOR® is a stable, neutral, odorless, anhydrous ointment base (Belersdorf Inc). While cooling, 1.26 g of the silver thiosulfate ion complexes of Example 1 were stirred into the melted AQUAPHOR® base. The stirring was continued until the silver thiosulfate ion complexes were homogeneously suspended. While stirring, the melted AQUAPHOR®/silver thiosulfate ion complexes composition was cooled to a semisolid base. The amount of silver in this silver-based antimicrobial composition was equivalent to 1.0% silver nitrate.

EXAMPLE 8
Stable Antimicrobial Composition—White Petrolatum USP

To illustrate an alternative silver-based antimicrobial composition of the present invention, 40 g of white petrolatum USP (Roundy's Pure Petroleum Jelly. White Petrolatum USP) was melted. While cooling, 2.52 g of the silver thiosulfate ion complexes of Example 1 were stirred into the melted white petrolatum base. The stirring was continued until the silver thiosulfate ion complexes were homogeneously suspended. While stirring, the melted white petrolatum/silver thiosulfate ion complexes composition was cooled to a semisolid base. The amount of silver in this silver-based antimicrobial composition was equivalent to 2.0% silver nitrate.

EXAMPLE 9
Stability of Anhydrous and Hydrated Antimicrobial Compositions

This example illustrates the instability of hydrated silver-based antimicrobial compositions comprising silver thiosulfate ion complexes. The experiments of this example utilize the compositions produced in Examples 6–8, as well as a composition containing a different base, VELVACHOL® [a neutral, hydrophilic cream, available from Owen Laboratories, which contains some water (amount unknown)] Cream.

EXAMPLE 9A
PEG Base Plus Water

A hydrated silver-based antimicrobial composition was made where the composition base was PEG. The composition was made by mixing 9 g of the silver-based antimicrobial composition of Example 6 with 1 ml of water. This silver-based antimicrobial composition contained approximately 10% water by weight.

EXAMPLE 9B
AQUAPHOR® Plus Water

A hydrated silver-based antimicrobial composition was made where the composition base was AQUAPHOR® (an ointment base comprising Petrolatum, Mineral Oil, Ceresin, and Lanolin Alcohol). The composition was made by mixing 9.5 g of the silver-based antimicrobial composition of Example 7 with 0.5 ml of water. This silver-based antimicrobial composition contained approximately 5% water.

EXAMPLE 9C
White Petrolatum Plus Water

A hydrated silver-based antimicrobial composition was made where the composition base was white petrolatum. The composition was made by mixing 9.5 g of the silver-based antimicrobial composition of Example 8 with 0.5 ml of water. This silver-based antimicrobial composition contained approximately 5% water.

EXAMPLE 9D
VELVACHOL® Cream

A silver-based antimicrobial composition containing 0.47 g of the silver thiosulfate ion complexes of Example 1 were stirred into 20 g of VELVACHOL® (Owen Laboratories). VELVACHOL® is a neutral, hydrophilic cream which contains some water (amount unknown). The amount of silver in this silver-based antimicrobial composition was equivalent to 1.0% silver nitrate.

The stability of the silver-based compositions of Examples 6, 7, 8, and 9A–D was evaluated over time. The stability of the compositions was determined by measuring the change of color, if any, when the compositions were stored in transparent containers in ambient light. Change of color indicates decomposition of the silver thiosulfate ion complexes. Table 1 below indicates the initial color of each composition and the change in color on days 7 and 14 and after 1 month.

As depicted by the results of this study, the silver-based compositions described in Examples 6, 7 and 8 demonstrated no change in color. In contrast, the hydrated silver-based compositions, Examples 9A–D, demonstrated major changes in color, some after only 7 days (Examples 9B and 9D); all of these compositions, i.e., Examples 9A–D, changed from their initial color to a brown or black color. Thus, the results of this study indicate that the anhydrous compositions of this invention were stable, while the analogous hydrated samples were not.

TABLE 1

Stability Of Silver-Based Compositions

Appearance Of Ointment

| Sample | Day 1 | Day 7 | Day 14 | Month 1 | Month 3 | Month 7 |
|---|---|---|---|---|---|---|
| Example 6: PEG Composition | Grayish White | No Change | No Change | No Change | No Change | No Change |
| Example 7: AQUAPHOR ® Composition | Slight Yellow | No Change | No Change | No Change | No Change | No Change |
| Example 8: White Petrolatum Composition | Slight Yellow | No Change | No Change | No Change | No Change | No Change |
| Example 9A: Hydrated PEG Composition | Grayish White | No Change | Slight Tan | Brown | Brown | Black |
| Example 9B: Hydrated AQUAPHOR ® Composition | Slight Yellow | Slight Tan | Brown | Dark Brown | Black | Black |

TABLE 1-continued

Stability Of Silver-Based Compositions

Appearance Of Ointment

| Sample | Day 1 | Day 7 | Day 14 | Month 1 | Month 3 | Month 7 |
|---|---|---|---|---|---|---|
| Example 9C: Hydrated White Petrolatum Composition | Slight Yellow | No Change | Tan | Black | Black | Black |
| Example 9D: VELVACHOL ® Cream | White | Tan | Brown | Black | Black | Black |

III. Antimicrobial Activity of Compositions Containing Silver Thiosulfate Ion Complexes

EXAMPLE 10

Antimicrobial Activity of Silver Thiosulfate Ion Complexes

The in vitro antimicrobial activity was evaluated by finding the minimum inhibitory concentration for the powder of silver thiosulfate ion complexes from Example 3. This powder was tested in serial two-fold dilutions ranging from 1.95 to 250 µg/ml. Broth microdilution was performed in serial dilution of the silver thiosulfate powder in tryptic soy broth (Difco). Each dilution was inoculated with 0.005 ml of a 24-hour growth of a microbe ($10^5$ to $10^7$ CFU/ml). After the dilutions were incubated at 37° C. overnight, the lowest dilution of the silver thiosulfate ion complexes that was without evidence of growth (i.e., was not cloudy) was the minimum inhibitory concentration (MIC) reported in terms of µg/ml.

The results shown in Table 2 demonstrate that the silver thiosulfate ion complexes powder has antimicrobial activity against both gram (+) and gram (−) microbes (Difco).

TABLE 2

| Isolate | ATCC Accession No. | Silver Thiosulfate Ion Complexes (µg/ml) |
|---|---|---|
| S. aureus | 25923 | <1.95 |
| S. epidermidis | 12228 | <1.95 |
| E. coli | 25922 | <1.95 |
| P. aeruginosa | 27853 | <1.95 |

EXAMPLE 11

Antimicrobial Activity of Silver-Based Compositions

The antimicrobial activity of the silver-based compositions of Examples 6, 7, and 8 were evaluated using a zone of inhibition (ZOI) protocol. In this ZOI protocol, 1 cm-diameter discs (Whatman Filter Paper, Quantitative 1) were coated with a thin layer of the compositions from Examples 6, 7, and 8. These coated discs were placed on Mueller Hinton Medium (MHM; Difco) with lawns of S. aureus (ATCC 25923; 24 hours growth from MHM plate). After incubation at 36° C. for 18 hours, the size of the zone of growth inhibition was measured (in mm) from the edge of the disc to the point of microbial growth. Table 3 shows the ZOI results for each composition on Day 1 and at one month.

TABLE 3

Antimicrobial Activity Of Silver-Based Compositions

| | Zone of Inhibition (mm) (S. aureus) | |
|---|---|---|
| Sample | Day 1 | 1 Month |
| Example 6: PEG Composition | 13.5 mm | 14.0 mm |
| Example 7: AQUAPHOR ® Composition | 10.0 mm | 13.0 mm |
| Example 8: White Petrolatum Composition | 10.0 mm | 10.5 mm |

As can be seen by the results of this study, the silver-based compositions of this invention (Examples 6, 7 and 8) demonstrated good antimicrobial activity that was stable for the duration of the study period. That is to say, the size of the zone of growth inhibition was essentially unchanged over the one month period.

IV. Use of Silver Thiosulfate Ion Complexes in Medical Devices

EXAMPLE 12

Foam Dressings Containing Silver Thiosulfate Ion Complexes

As previously indicated, the silver thiosulfate ion complexes of the present invention can be used in conjunction with medical devices. This example illustrates the use of silver thiosulfate ion complexes to prepare a medical device made up of a foam polymer matrix. In this example, the complexes were incorporated into the matrix during the manufacturing of the polymer matrix.

A foam dressing was produced by first dissolving 0.54 g of silver thiosulfate ion complexes powder in 150 ml of a 0.5% Pluronic L-62 (BASF) aqueous solution. This solution was the mixed with 140 g of a polyurethane prepolymer (Hypol 2002, Hampshire) in a 1-liter disposable plastic beaker. The resulting mixture instantly began to react to form a foam. After 10 minutes the foam was removed from its container and sliced to produce individual foam dressings (approximately 7.5 cm in diameter. The slices of foam dressings were dried at 50° C. in a dark convection oven.

These foam dressings were light stable and antimicrobially active. In this example and Examples 13–18 that follow, the terms "light stable," "photostable," and the like mean that the samples did not discolor after 72 hours of exposure to ambient room light. In this example and Examples 13–18 that follow, the term "antimicrobially active" means that a small piece (nominally 1 cm×1 cm or 1 cm strands in the case of alginate fibers) produced zones of inhibition when placed on both a lawn of S. aureus (ATCC 25923) and a lawn of E. coli (ATCC 25922). The lawns were produced by plating 24-hour growth microbes on MHM plates; after incubation for 24 hours, each sample was examined to determine whether a zone of inhibition was present.

This foam dressing can be used for a large variety of medical applications, including as an antimicrobial absorptive foam dressing.

EXAMPLE 13

Foam Dressing Containing Silver Thiosulfate Ion Complexes

This example further illustrates the use of silver thiosulfate ion complexes to prepare a medical device made up of a foam polymer matrix. In contrast to the previous example, the silver thiosulfate ion complexes were incorporated into polymer matrix following the matrix' manufacture.

In this example, a foam dressing (Hydrasorb® Sponge Foam Dressing (10 cm×10 cm); Avitar) was submerged in an aqueous solution containing silver thiosulfate ion complexes powder from Example 3 (0.1 g per liter). The foam dressing samples were removed and dried at 50° C. in a convection oven. These silver thiosulfate ion complexes-containing foam dressings were light stable and antimicrobially active. As indicated in the previous example, these foam dressings can be used for a large variety of medical applications, including as an antimicrobial absorptive foam dressings.

EXAMPLE 14
Hydrocolloid Dressing Containing Silver Thiosulfate Ion Complexes This example illustrates the use of the silver thiosulfate ion complexes to prepare a medical device which is made up of a hydrocolloid absorbent polymer matrix. In this example, the complexes were incorporated into the matrix during the manufacturing of the polymer matrix.

A hydrocolloid dressing containing silver thiosulfate ion complexes was produced by first thoroughly mixing 0.157 g of silver thiosulfate ion complexes powder (mesh>100) from Example 1 with 10.0 g of sodium carboxymethyl cellulose (Aldrich). Thereafter, 4 g of this treated carboxymethyl cellulose was mixed thoroughly with 4 g of a polyurethane prepolymer (Aquapol 035-0031, Cook Composites and Polymers). This mixture was then pressed between a polyurethane film and a silicone-treated hydrocolloid matrix and was allowed to cure for 24 hours.

The resulting silver thiosulfate ion complexes-containing hydrocolloid dressing was photostable and antimicrobially active. This type of dressing is useful on exudating, malodorous wounds.

EXAMPLE 15
Hydrocolloid Dressing Containing Silver Thiosulfate Ion Complexes This example further illustrates the use of silver thiosulfate ion complexes of this invention to prepare a medical device which is made up of an hydrocolloid absorbent polymer matrix. However, in this example the silver thiosulfate ion complexes were incorporated into the polymer matrix by a different procedure than that presented in the preceding example.

The hydrocolloid dressing was produced by first dissolving 0.157 g of a silver thiosulfate ion complexes powder (mesh>100) from Example 1 in 10.0 ml of water. To this solution was added 100 g of sodium carboxymethyl cellulose (Aldrich, Milwaukee, Wis.) which absorbed the solution. The treated sodium carboxymethyl cellulose was allowed to dry at room temperature. Thereafter, 4 g of the dried treated carboxymethyl cellulose was mixed thoroughly with 4 g of a polyurethane prepolymer (Aquapol 035-0031, Cook Composites and Polymers). This mixture was then pressed between a polyurethane film and a silicone treated liner and was allowed to cure for 24 hours.

As with the silver thiosulfate ion complexes-containing hydrocolloid dressing produced in the preceding example, the hydrocolloid dressing is photostable and antimicrobially active and is useful on exudating, malodorous wounds.

EXAMPLE 16
Adhesive Films Containing Silver Thiosulfate Ion Complexes

This example illustrates the use of silver thiosulfate ion complexes to produce adhesive films. Specifically, a pressure sensitive adhesive (PSA) containing silver thiosulfate ion complexes was produced in this example. Adhesive films are, among other things, especially useful in covering painful abrasive-type skin wounds and partial skin graft sites.

The silver thiosulfate ion complexes-containing PSA was made by mixing 0.25 g of the silver thiosulfate ion complexes powder from Example 1 in An adhesive solution consisting of 45 g of a proprietary medical grade acrylic based latex (58% solids) (Avery Dennison, Inc.) and 5 g polyethylene glycol (M.W. 600) (Aldrich) was first prepared. Then, 0.25 g of the silver thiosulfate ion complexes powder from Example 1 was mixed with the adhesive solution, forming an adhesive mixture. This adhesive mixture, when coated and dried, produces a tacky, adhesive film.

The adhesive film is photostable and antimicrobially active. This adhesive film can be laminated to dressing backing materials to produce dressings which are antimicrobially active. Dressings with the silver thiosulfate ion complexes-containing PSA are especially useful in covering painful abrasive-type skin wounds and partial skin graft sites.

EXAMPLE 17
Alginate Materials Containing Silver Thiosulfate Ion Complexes

This example illustrates the use of silver thiosulfate ion complexes to produce a medical device which is made up of non-adherent alginate material. Specifically, the method of this example involves the use of a calcium chloride bath which results in crosslinked alginate fibers that incorporate the silver thiosulfate ion complexes.

First, water-swellable alginate fibers were produced containing silver thiosulfate ion complexes. The alginate fibers were made by using a syringe to inject a 5% sodium alginate solution (Pronova LV M Sodium alginate, Protan) into a bath consisting of a 10% calcium chloride solution (Aldrich, deionized water as diluent) containing 0.1 g/liter silver thiosulfate ion complexes powder from Example 3. The alginate solution immediately formed water-insoluble alginate fibers upon contact with the calcium chloride/silver thiosulfate ion complexes bath. The fibers were pulled from the bath and allowed to dry (50° C.).

The resulting fibers are photostable and antimicrobially active. These fibers can be used to make antimicrobial alginate dressings and tamponades. Alginate materials containing silver thiosulfate ion complexes are especially useful in covering painful abrasive-type skin wounds and wound ulcers as well as for filling in deep wounds and cavities.

EXAMPLE 18
Alginate Materials Containing Silver Thiosulfate Ion Complexes

To further illustrate the use of the silver thiosulfate ion complexes of this invention to produce a medical device which is made up on non-adherent alginate material, this example utilizes a method that does not include a calcium chloride bath.

First, an aqueous solution containing 0.1 g/liter of a silver thiosulfate ion complexes from Example 3 was prepared. The resulting aqueous solution was then applied to a 9.5 cm×9.5 cm alginate dressing (Steriseal Sorbsan Surgical Dressing, Steriseal) by spraying the solution onto the dressing. Alternatively, the silver thiosulfate ion complexes solution can be applied by clipping the alginate dressing into the solution. The alginate fibers of the dressing absorbed the applied solution; thereafter, the treated alginate dressing was allowed to dry (room temperature).

The alginate dressing was light stable and was antimicrobially active, and, as noted in the preceding example, it is especially useful for malodorous wounds as well as for covering painful abrasive-type skin wounds and wound ulcers.

V) Use of Silver Thiosulfate Ion Complexes in Combination with Other Medicinal Agents

EXAMPLE 19
Pharmaceutical Composition Combining Mupirocin With Silver Thiosulfate Ion Complexes To illustrate an antimicrobial pharmaceutical composition consisting of a combination of the silver thiosulfate ion complexes of the present invention with one or more agents, 0.02 g of the silver thiosulfate ion complexes from Example 2 were blended into 2.0 g of a mupirocin ointment (BACTROBAN® [2% mupirocin acid in a PEG base], SmithKline Beecham). The mupirocin ointment is a topical antimicrobial with excellent gram (+) antimicrobial properties. The silver thiosulfate ion complexes were blended into the mupirocin ointment by first melting the mupirocin ointment and then stirring the silver thiosulfate ion complexes into the melted ointment. The ointment was stirred continually until it cooled and resolidified.

EXAMPLE 20
Pharmaceutical Composition Combining Mafenide With Silver Thiosulfate Ion Complexes To further illustrate an antimicrobial pharmaceutical composition consisting of a combination of the silver thiosulfate ion complexes of this invention with one or more agents, 0.25 g of mafenide (Sigma) ($\alpha$-aminomethylbenzesulfonamide) and 0.25 g of the silver thiosulfate ion complexes of Example 3 were blended into 24.50 g of a PEG composition ("PEG Composition"); the PEG Composition was produced by melting together a blend of 40% PEG (M.W. 3450) and 60% PEG (M.W. 600). The pharmaceutical composition was produced by first melting the PEG Composition and then stirring in the silver thiosulfate ion complexes and mafenide. The resulting pharmaceutical composition was stirred continually until cooled and resolidified. The resulting pharmaceutical composition has use as a broad spectrum topical antimicrobial.

EXAMPLE 21
Pharmaceutical Composition Combining Metronidazole With Silver Thiosulfate Ion Complexes To further illustrate an antimicrobial pharmaceutical composition consisting of a combination of the silver thiosulfate ion complexes of the present invention with one or more agents, 0.25 g of metronidazole (Sigma) and 0.25 g of the silver thiosulfate ion complexes of Example 3 were blended into 24.50 g of a PEG composition ("PEG Composition"); the PEG Composition was produced by melting together a blend of 40% PEG (M.W. 3450) and 60% PEG (M.W. 600). The pharmaceutical composition was produced by first melting the PEG Composition and then stirring in the silver thiosulfate ion complexes and metronidazole. The resulting pharmaceutical composition was stirred continually until it cooled and resolidified. This pharmaceutical composition has use as a broad spectrum topical antimicrobial and is especially useful in the treatment of malodorous wounds.

EXAMPLE 22
Pharmaceutical Composition Combining Chlorhexidine With Silver Thiosulfate Ion Complexes To further illustrate an antimicrobial pharmaceutical composition consisting of a combination of the silver thiosulfate ion complexes of the present invention with one or more agents, 0.25 g of chlorhexidine diacetate hydrate (Aldrich) and 0.25 g of the silver thiosulfate ion complexes of Example 3 were blended into 24.5 g of AQUAPHOR® (a cholesterolized absorbent EUCERITE® ointment base produced by Belersdorf Inc.). The pharmaceutical composition was produced by first melting the AQUAPHOR® ointment and then stirring in the silver thiosulfate ion complexes and chlorhexidine. The resulting pharmaceutical composition was stirred continually until it cooled and resolidified. This pharmaceutical composition has use as a broad spectrum topical antimicrobial.

EXAMPLE 23
Pharmaceutical Composition Combining Triclosan With Silver Thiosulfate Ion Complexes To further illustrate an antimicrobial pharmaceutical composition consisting of a combination of the silver thiosulfate ion complexes of the present invention with one or more medicinal agents, 0.50 g of triclosan (Irgasan DP 300, Ciba-Geigy, Greensboro, N.C.) and 0.50 g of the silver thiosulfate ion complex of Example 3 were blended into 24.00 g of AQUAPHOR® (a cholesterolized absorbent EUCERITE® ointment base produced by Belersdorf Inc.). The pharmaceutical composition was produced by first melting the AQUAPHOR® ointment and then stirring in the silver thiosulfate ion complexes and triclosan. The resulting pharmaceutical composition was stirred continually until it cooled and resolidified. This pharmaceutical composition has use as a broad spectrum topical antimicrobial.

EXAMPLE 24
Pharmaceutical Composition Combining Hydrocortisone With Silver Thiosulfate Ion Complexes To further illustrate an antimicrobial pharmaceutical composition consisting of a combination of the silver thiosulfate ion complexes of the present invention with one or more agents, 0.50 g of Hydrocortisone 21-Acetate (Sigma) and 0.50 g of the silver thiosulfate ion complexes of Example 3 were blended into 24.00 g of AQUAPHOR® (a cholesterolized absorbent EUCERITE® ointment base produced by Belersdorf Inc.). The pharmaceutical composition was produced by first melting the AQUAPHOR® ointment and then stirring in the silver thiosulfate ion complexes and hydrocortisone. The resulting pharmaceutical composition was stirred continually until it cooled and resolidified. This pharmaceutical composition has use topically as an anti-inflammatory and an anti-itch treatment which also has antimicrobial properties to prevent a secondary infection when applied topically to blistered wounds caused by dermatitis, insect bites, poison ivy, etc.

EXAMPLE 25
Pharmaceutical Composition Combining Lidocaine With Silver thiosulfate Ion Complexes To further illustrate an antimicrobial pharmaceutical composition consisting of a combination of the silver thiosulfate ion complexes of the present invention with one or more agents, 0.50 g of lidocaine (Sigma) and 0.50 g of the silver thiosulfate ion complexes of Example 3 were blended into 24.00 g of PEG composition ("PEG Composition"); the PEG Composition was produced by melting together a blend of 40% PEG (M.W. 3450) and 60% PEG (M.W.). The pharmaceutical composition was produced by first melting the PEG Composition and then stirring in the silver thiosulfate ion complexes and lidocaine. The resulting pharmaceutical composition was stirred continually until it cooled and resolidified. This pharmaceutical composition has use as a topical anesthetic which also has antimicrobial properties to prevent a secondary infection when applied to exposed tissues or wounds.

EXAMPLE 26
Pharmaceutical Composition Combining Pramoxine With Silver Thiosulfate Ion Complexes To further illustrate an antimicrobial pharmaceutical composition consisting of a combination of the silver thiosulfate ion complexes of the present invention with one or more agents, 1.00 g of pramoxine hydrochloride (Sigma) and 0.50 g of the silver thiosulfate ion complexes of Example 3 were blended into 23.50 g of PEG composition ("PEG Composition"); the PEG Composition was produced by melting together a blend of 40% PEG (M.W. 3450) and 60% PEG (M.W. 600). The pharmaceutical composition was produced by first melting the PEG Composition and then stirring in the silver thiosulfate ion complexes and pramoxine. The resulting pharmaceutical composition was stirred continually until it cooled and resolidified. This pharmaceutical composition has use as a topical anesthetic which also has antimicrobial properties to prevent a secondary infection when applied to exposed tissues or wounds.

From the above, it should be evident that the present invention provides for silver-based antimicrobial compositions and processes for making such compositions that are suitable for use in the treatment and prevention of infections. It should be understood that the present invention is not limited to the specific compositions shown nor to the uses of the compositions described. In light of the foregoing disclosure, it will be apparent to those skilled in the art that substitutions, alterations, and modifications are possible in the practice of this invention without departing from the spirit or scope thereof.

I claim:

1. An antimicrobial compositions, comprising silver thiosulfate ion complexes in a base.

2. The composition of claim 1, wherein said silver thiosulfate ion complexes are homogeneously suspended in said base.

3. The composition of claim 1, wherein said base is anhydrous.

4. The composition of claim 1, wherein the concentration of said silver thiosulfate ion complexes within said base is from 0.01% to 30% (w/w).

5. The composition of claim 1, wherein the concentration of said silver thiosulfate ion complexes within said base is from 0.1% to 3.0% (w/w).

6. The composition of claim 1, wherein the concentration of said silver thiosulfate ion complexes within said base is from 0.2% to 1.5% (w/w).

7. The composition of claim 1, wherein said base is selected from the group consisting of polyethylene glycol, AQUAPHOR®, and white petrolatum.

8. The composition of claim 1, wherein said silver thiosulfate ion complexes are derived from the complexation of a silver cation from silver halides with anions.

9. The composition of claim 8, wherein said silver halides comprises silver chloride and said anions comprise sodium thiosulfate salts.

10. The composition of claim 9, wherein the molar ratio of the thiosulfate anions to silver cations is at least 1:1.

11. The composition of claim 9, wherein the molar ratio of thiosulfate anions to silver cations is at least 1.3:1.

12. A pharmaceutical mixture, comprising:
 a) a medicinal agent; and
 b) silver thiosulfate ion complexes.

13. The pharmaceutical mixture of claim 12, wherein said silver thiosulfate ion complexes are carrier-free.

14. The pharmaceutical mixture of claim 12, further comprising an anhydrous base.

15. The composition of claim 13, wherein said base is selected from the group consisting of polyethylene glycol, AQUAPHOR®, and white petrolatum.

16. The pharmaceutical mixture of claim 12 wherein the concentration of said silver thiosulfate ion complexes in said pharmaceutical mixture is from 0.01% to 30% (w/w).

17. The pharmaceutical mixture of claim 12, wherein the concentration of said silver thiosulfate ion complexes in said pharmaceutical mixture is from 0.1% to 3.0% (w/w).

18. The pharmaceutical mixture of claim 12, wherein the concentration of said silver thiosulfate ion complexes in said mixture is from 0.2% to 1.5% (w/w).

19. The pharmaceutical mixture of claim 12, wherein said medicinal agent of said pharmaceutical mixture is an antimicrobial agent.

20. The pharmaceutical mixture of claim 19, wherein said antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline.

21. The pharmaceutical mixture of claim 12, wherein said medicinal agent of said pharmaceutical mixture is a steroid.

22. The pharmaceutical mixture of claim 21, wherein said steroid is selected from the group consisting of betamethasone benzoate, betamethasone valerate, desonide, fluocinolone acetonide, halcinonide, hydrocortisone, and metandienone.

23. The pharmaceutical mixture of claim 12, wherein said medicinal agent of said pharmaceutical mixture is an anesthetic.

24. The pharmaceutical mixture of claim 23, wherein said anesthetic is selected from the group consisting of benzocaine, dibucaine, lidocaine, pramoxine hydrochloride and tetracacine.

25. A method of treating or preventing a microbial infection, comprising:
 a) providing:
  i) a subject, said subject either infected or at risk of infection by a topical microbial infection, and
  ii) an effective amount of carrier-free suspended silver thiosulfate ion complexes in a base to form a pharmaceutical mixture; and
 b) administering the effective amount of the carrier-free suspended silver thiosulfate ion complexes in a base to the subject.

26. The method of claim 25, wherein said silver thiosulfate ion complexes are carrier-free.

27. The method of claim 25, wherein said base is anhydrous.

28. The composition of claim 27, wherein said base is selected from the group consisting of polyethylene glycol, AQUAPHOR®, and white petrolatum.

29. The method of claim 25 wherein the concentration of said silver thiosulfate ion complexes in said pharmaceutical mixture is from 0.01% to 30% (w/w).

30. The method of claim 25, wherein the concentration of said silver thiosulfate ion complexes in said pharmaceutical mixture is from 0.1% to 3.0% (w/w).

31. The method of claim 25, wherein the concentration of said silver thiosulfate ion complexes in said mixture is from 0.2% to 1.5% (w/w).

32. The method of claim 25, wherein said pharmaceutical mixture further comprises a medicinal agent.

33. The method of claim 32, wherein said medicinal agent is a microbial agent.

34. The method of claim 33, wherein said antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline.

35. The method of claim 32, wherein said medicinal agent of said pharmaceutical mixture is a steroid.

36. The method of claim 35, wherein said steroid is selected from the group consisting of betamethasone benzoate, betamethasone valerate, desonide, fluocinolone acetonide, halcinonide, hydrocortisone, and metandienone.

37. The method of claim 32, wherein said medicinal agent of said pharmaceutical mixture is an anesthetic.

38. The method of claim 37, wherein said anesthetic is selected from the group consisting of benzocaine, dibucaine, lidocaine, pramoxine, hydrochloride and tetracacine.

* * * * *